US010316165B2

(12) United States Patent
King et al.

(10) Patent No.: US 10,316,165 B2
(45) Date of Patent: Jun. 11, 2019

(54) NON-HALOGENATED FLAME RETARDANT HINDERED AMINE LIGHT STABILIZER CROSS-LINKERS

(71) Applicant: International Business Machines Corporation, Armonk, NY (US)

(72) Inventors: Scott B. King, Rochester, MN (US); Brandon M. Kobilka, Tucson, AZ (US); Joseph Kuczynski, North Port, FL (US); Jason T. Wertz, Pleasant Valley, NY (US)

(73) Assignee: International Business Machines Corporation, Armonk, NY (US)

( * ) Notice: Subject to any disclaimer, the term of this patent is extended or adjusted under 35 U.S.C. 154(b) by 0 days.

(21) Appl. No.: 15/711,048

(22) Filed: Sep. 21, 2017

(65) Prior Publication Data

US 2019/0085149 A1 Mar. 21, 2019

(51) Int. Cl.
*C07D 211/44* (2006.01)
*C07D 211/58* (2006.01)
*C07C 211/09* (2006.01)
*C08K 5/00* (2006.01)
*C07F 9/09* (2006.01)
*C07F 9/22* (2006.01)

(52) U.S. Cl.
CPC .......... *C08K 5/0066* (2013.01); *C07C 211/09* (2013.01); *C07D 211/44* (2013.01); *C07D 211/58* (2013.01); *C07F 9/095* (2013.01); *C07F 9/222* (2013.01)

(58) Field of Classification Search
CPC .... C07D 211/44; C07D 211/58; C07C 211/09
See application file for complete search history.

(56) References Cited

U.S. PATENT DOCUMENTS

| 4,824,884 | A | 4/1989 | MacLeay et al. |
| 4,857,595 | A | 8/1989 | Kazmierzak et al. |
| 4,863,999 | A | 9/1989 | MacLeay et al. |
| 5,145,893 | A | 9/1992 | Galbo et al. |
| 5,981,635 | A | 11/1999 | Hayes |
| 5,990,209 | A | 11/1999 | Rubino et al. |
| 10,030,090 | B1 | 7/2018 | King et al. |
| 10,125,206 | B1 | 11/2018 | King et al. |
| 2010/0324182 | A1 | 12/2010 | Roth |
| 2011/0223419 | A1 | 9/2011 | Okawara et al. |
| 2012/0245318 | A1 | 9/2012 | Nakaya et al. |
| 2013/0059952 | A1 | 3/2013 | Pfaendner et al. |
| 2014/0203226 | A1 | 7/2014 | Takenaka et al. |
| 2016/0176855 | A1 | 6/2016 | Kröhnke et al. |
| 2016/0229989 | A1 | 8/2016 | Lips et al. |

FOREIGN PATENT DOCUMENTS

| CA | 1 227 598 A | 9/1987 |
| EP | 0 084 882 A1 | 8/1983 |
| EP | 0 337 431 A2 | 10/1989 |
| EP | 0 499 581 A1 | 2/1991 |
| JP | 63152610 A | 6/1988 |
| JP | 10176016 A | 6/1998 |
| JP | 2001-026623 A | 1/2001 |
| JP | 2003-066561 A | 3/2003 |
| JP | 2003-137947 A | 5/2003 |
| JP | 2003-192742 A | 7/2003 |
| JP | 2010-020866 A | 1/2010 |
| JP | 2010-042517 A | 2/2010 |
| JP | 2010-044097 A | 2/2010 |
| JP | 2016-117865 A | 6/2016 |
| WO | WO-1996/021696 A1 | 7/1996 |
| WO | WO-2010/016376 A1 | 2/2010 |
| WO | WO-2010/074066 A1 | 7/2010 |
| WO | WO-2011/086114 A1 | 7/2011 |

OTHER PUBLICATIONS

Appendix P; List of IBM Patent or Applications Treated as Related, Sep. 21, 2017, 2 pages.
PVC, *Property modification of PVC products*, pvc.org (online), accessed Apr. 19, 2017, 5 pages, URL: www.pvc.org/en/p/property-modification-of-pvc-products.
EFRA, *Flame Retardant types and applications—What is the mode of action of flame retardants?*, Flame Retardants—Frequently Asked Questions, pp. 14, The European Flame Retardants Association (online), accessed Apr. 19, 2017, URL: www.flameretardants-online.com/images/itempics/2/9/1/item_18192_pdf_1.pdf.
SciFinder, Results of SciFinder Search of Polymetric Materials, Feb. 2017, SciFinder.com (online), 11 pages, American Chemical Society (ACS), Washington, D.C.
U.S. Appl. No. 15/673,500, to Scott B. King et al., entitled, *Non-Halogenated Flame Retardant Hindered Amine Light Stabilizer Impact Modifiers*, assigned to International Business Machines Corporation, 79 pages.
U.S. Appl. No. 15/814,947, to Scott B. King et al., entitled, *Non-Halogenated Flame Retardant Hindered Amine Light Stabilizer Impact Modifiers*, assigned to International Business Machines Corporation, 79 pages.
Coiai et al., *Post-polymerization modification by nitroxide radical coupling*, Polymer International, Jun. 2018, 37 pages, Society of Chemical Industry, wileyonlinelibrary.com, DOI: 10.1002/pi.5664.
U.S. Appl. No. 16/107,135, to Scott B. King et al., entitled, *Non-Halogenated Flame Retardant Hindered Amine Light Stabilizer Impact Modifiers*, assigned to International Business Machines Corporation, 79 pages.
Appendix P; List of IBM Patent or Applications Treated as Related, Nov. 12, 2018, 2 pages.
Sabo, *Hindered Amine Light Stabilizers*, Sabo.com (online), accessed Mar. 6, 2017, 2 pages, URL: www.sabo.com/sabo/products_and_markets.php?market_id=5&family_id=37.

(Continued)

*Primary Examiner* — Sun Jae Yoo
(74) *Attorney, Agent, or Firm* — James L. Olsen

(57) ABSTRACT

A process a process of forming a non-halogenated flame retardant (FR) hindered amine light stabilizer (HALS) cross-linker is disclosed. The process includes forming a mixture that includes a first molecule having a hindered amine group. The first molecule corresponds to a functionalized 2,2,6,6-tetramethylpiperidine (TMP) molecule. The process also includes forming the non-halogenated FR HALS cross-linker via a chemical reaction of the first molecule a second molecule. The second molecule includes a phosphoryl group, a chloride group, and at least one cross-linkable (CL) moiety.

3 Claims, 16 Drawing Sheets

(56) References Cited

OTHER PUBLICATIONS

Donohue, *Hindered Amine Light Stabilizers Form Cytotoxic Hydroxylamines as they Protect the Polymer from Radiation Damage Without Discoloration*, Figure 36 of 56, Micro ftir5-Measuring radiation effects, durometer, SlideShare.net (online), Dec. 7, 2015, 1 page, URL: www.slideshare.net/JohnDonohue2/micro-ftir5measuring-radiation-effectsdurometer.

Gray et al., *The Influence of Flame Retardant Structure on UV Stabilization Approaches in Polypropylene*, Journal of Vinyl & Additive Technology, vol. 2, No. 1, Mar. 1996, pp. 63-68, John Wiley and Sons, Hoboken, NY.

Gijsman et al., *Hindered amine light stabilizers: An alternative for radiation cross-linked UHMwPE implants*, Biomaterials, vol. 31, Issue 26, Sep. 2010, pp. 6685-6691, ScienceDirect.com (online), Elsevier Ltd, the Netherlands.

Dintcheva et al., *Multi-functional hindered amine light stabilizers-functionalized carbon nanotubes for advanced ultra-high molecular weight Polyethylene-based nanocomposites*, Composites Part B: Engineering, vol. 82, Dec. 2015, pp. 196-204, ScienceDirect.com (online), Elsevier Ltd, the Netherlands.

Desai et al., *A novel photoadditive for polyolefin photostabilization: hindered amine light stabilizer*, Macromolecular Symposia, vol. 169, Issue 1, May 2001, pp. 121-128, Wiley-VCH Verlag GmbH & Co. KGaA, Weinheim.

Ávár et al., *Studies on the interaction of photoreactive light stabilizers and UV-absorbers*, Progress in Organic Coatings, vol. 35, Issues 1-4, pp. 11-17, ScienceDirect.com (online), Elsevier Ltd, the Netherlands.

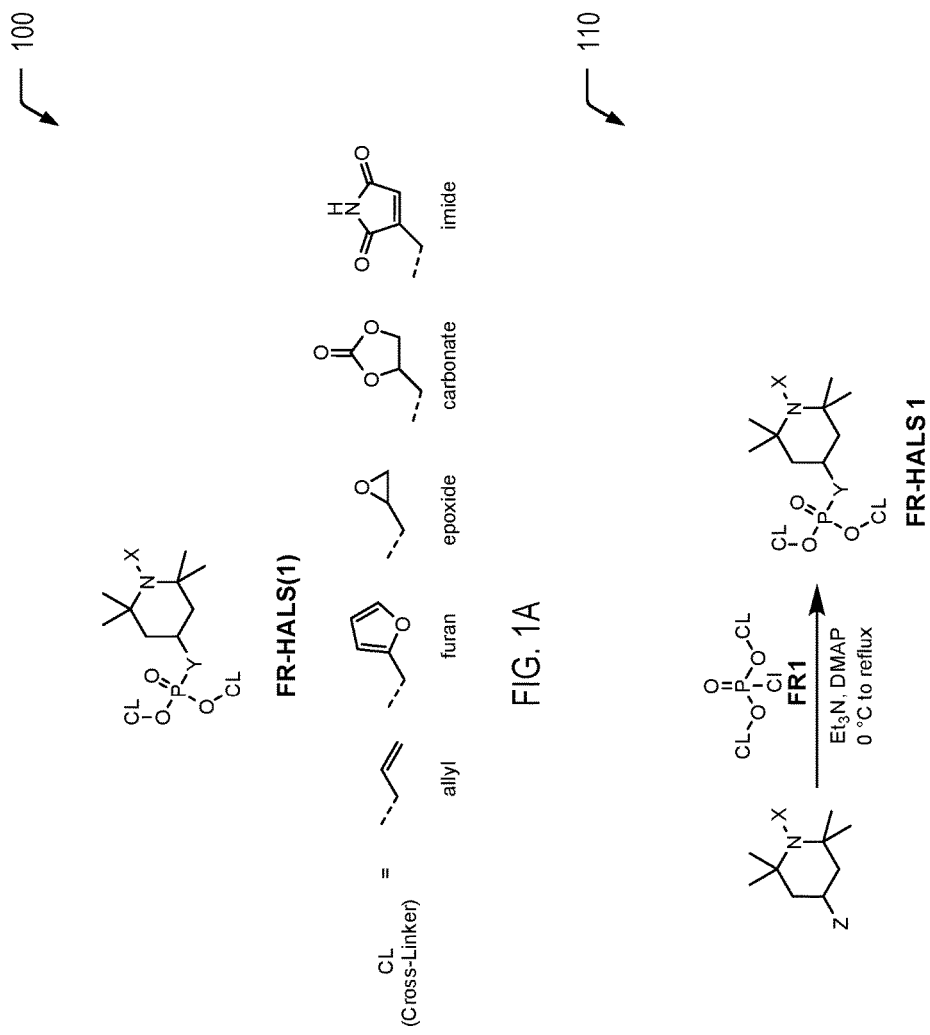

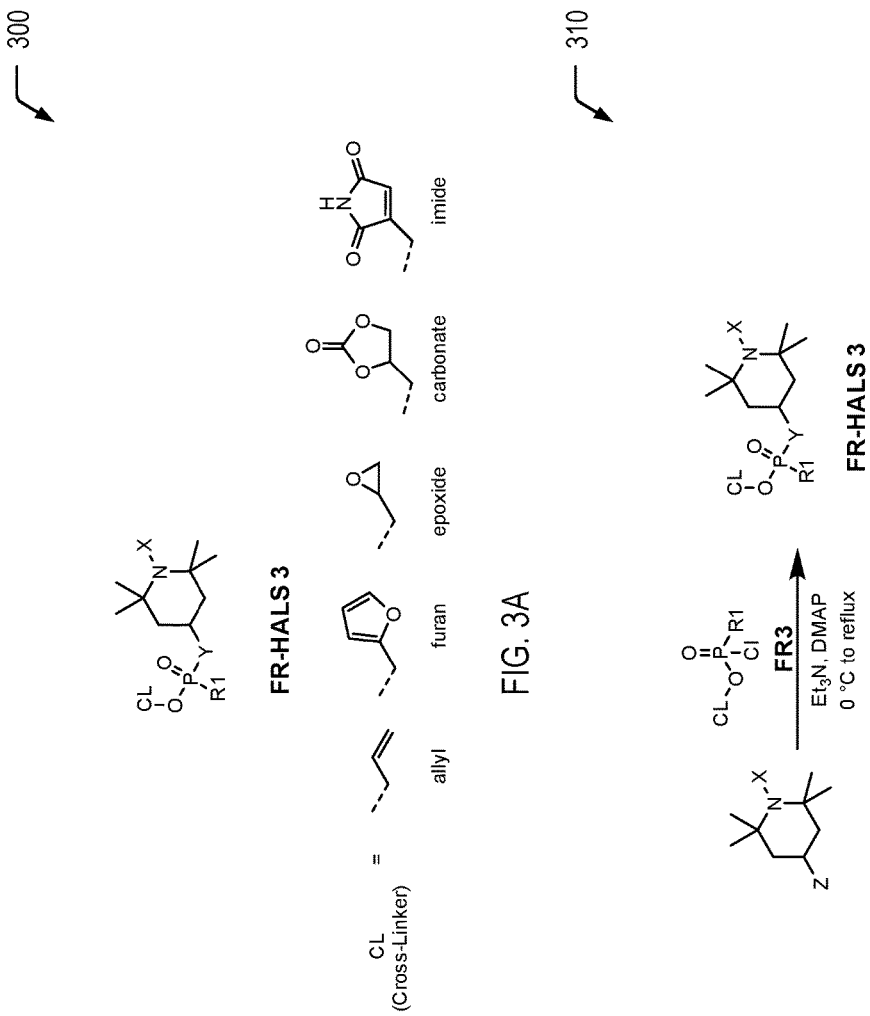

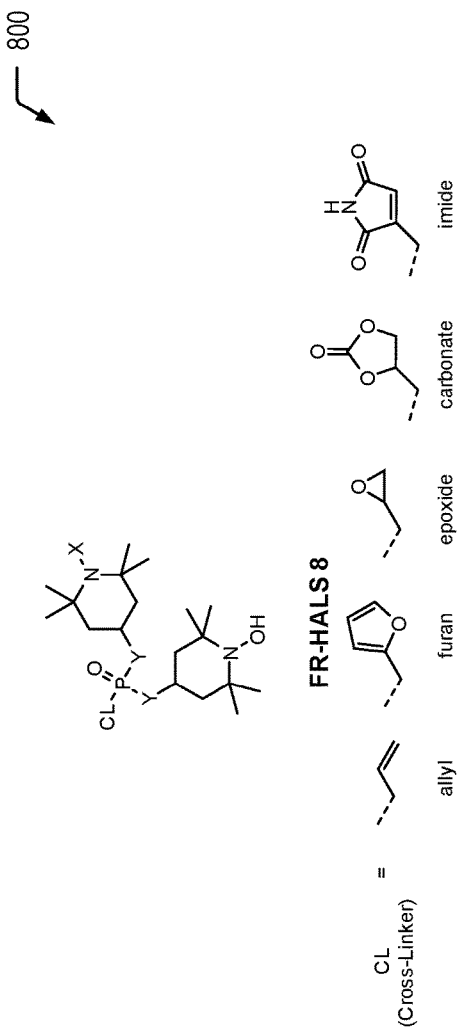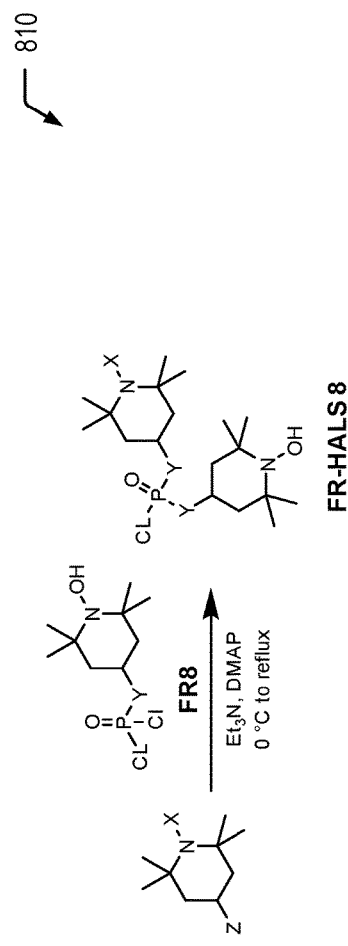
FIG. 8A
FIG. 8B

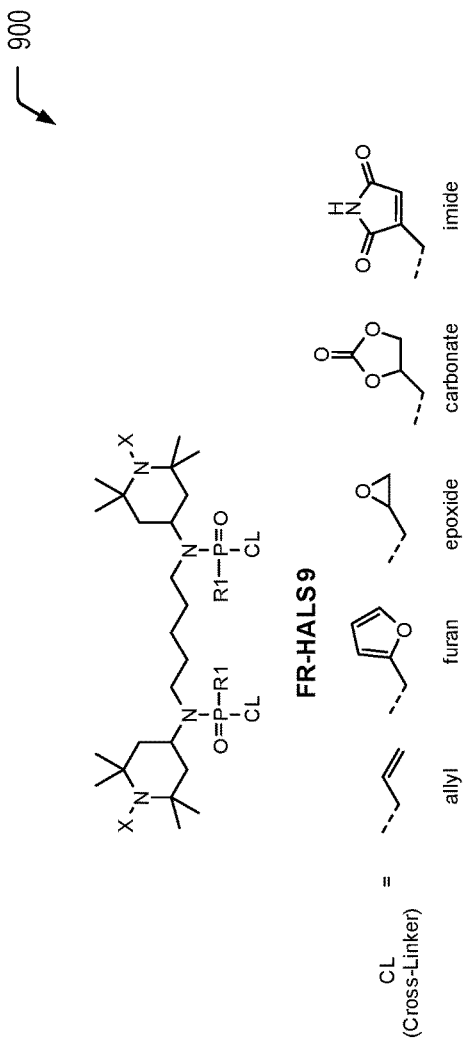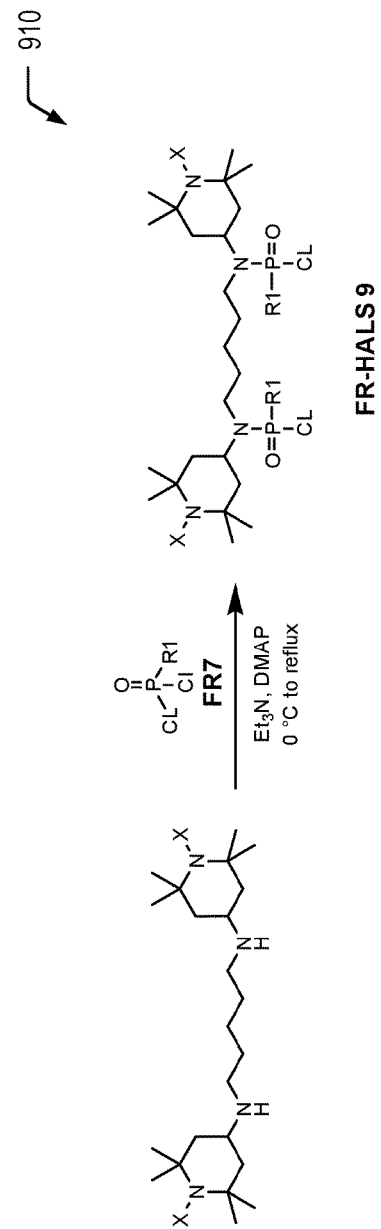
FIG. 9A
FIG. 9B

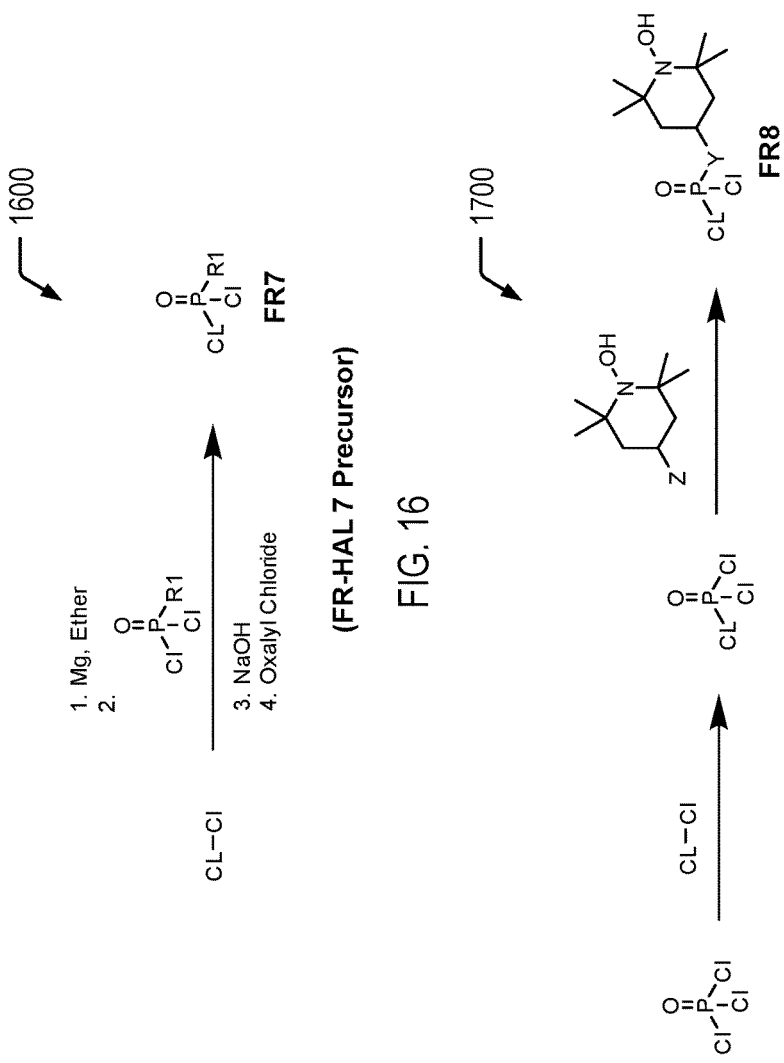

NON-HALOGENATED FLAME RETARDANT HINDERED AMINE LIGHT STABILIZER CROSS-LINKERS

BACKGROUND

Hindered amine light stabilizer ("HALS") molecules may be added to a polymer in order to protect the polymer from radiation damage, such as ultraviolet (UV) degradation of the polymer. HALS molecules are believed to provide protection from radiation damage by terminating photo-oxidation processes in polymers through chemical reaction with free radical and peroxide intermediates. A common approach to render a polymer flame retardant is by incorporation of additives such as halogenated (e.g., brominated) materials. In some cases, brominated flame retardant additives may release bromine radicals that may react directly with the HALS molecules or may abstract a hydrogen from the polymer matrix and deactivate the HALS molecules through an acid-base reaction. The result is loss of light stabilization and rapid UV degradation of the unprotected polymer.

SUMMARY

According to an embodiment, a process of forming a non-halogenated flame retardant (FR) hindered amine light stabilizer (HALS) cross-linker is disclosed. The process includes forming a mixture that includes a first molecule having a hindered amine group. The first molecule corresponds to a functionalized 2,2,6,6-tetramethylpiperidine (TMP) molecule having the following formula:

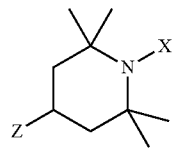

In the above formula, X corresponds to an oxyl radical (O.), a hydroxyl (OH) group, or an alkoxy/aryloxy (O—R2) group, and Z corresponds to a hydroxyl (OH) group, an amine (NH$_2$) group, or an alkyl/aryl amine (NH—R3) group. The process also includes forming the non-halogenated FR HALS cross-linker via a chemical reaction of the first molecule with a second molecule. The second molecule includes a phosphoryl group, a chloride group, and at least one cross-linkable (CL) moiety.

According to another embodiment, a process of forming a non-halogenated FR HALS cross-linker is disclosed. The process includes forming a mixture that includes an FR molecule that includes a phosphoryl group, a chloride group, and at least one CL moiety. The process also includes forming the non-halogenated FR HALS cross-linker via a chemical reaction of the FR molecule and a functionalized 2,2,6,6-tetramethylpiperidine (TMP) molecule having the following formula:

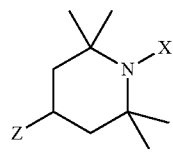

In the above formula, X corresponds to an oxyl radical (O.), a hydroxyl (OH) group, or an alkoxy/aryloxy (O—R2) group, and Z corresponds to a hydroxyl (OH) group, an amine (NH$_2$) group, or an alkyl/aryl amine (NH—R3) group.

According to yet another embodiment, a non-halogenated FR HALS cross-linker is formed according to a process that includes chemically reacting a first molecule having a hindered amine group with a second molecule that includes a phosphoryl group, a chloride group, and at least one cross-linkable (CL) moiety. The first molecule corresponds to a functionalized 2,2,6,6-tetramethylpiperidine (TMP) molecule having the following formula:

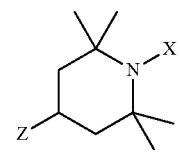

In the above formula, X corresponds to an oxyl radical (O.), a hydroxyl (OH) group, or an alkoxy/aryloxy (O—R2) group, and Z corresponds to a hydroxyl (OH) group, an amine (NH$_2$) group, or an alkyl/aryl amine (NH—R3) group.

The foregoing and other objects, features, and advantages of the invention will be apparent from the following more particular descriptions of exemplary embodiments of the invention as illustrated in the accompanying drawings wherein like reference numbers generally represent like parts of exemplary embodiments of the invention.

BRIEF DESCRIPTION OF THE DRAWINGS

FIG. 1A is a diagram depicting a first non-halogenated FR HALS cross-linker of the present disclosure, according to one embodiment.

FIG. 1B is a chemical reaction diagram illustrating an example of a process of utilizing a first FR molecule that includes a phosphorus-based FR moiety and cross-linkable (CL) moieties to form the first non-halogenated FR HALS cross-linker depicted in FIG. 1A, according to one embodiment.

FIG. 3A is a diagram depicting a third non-halogenated FR HALS cross-linker of the present disclosure, according to one embodiment.

FIG. 3B is a chemical reaction diagram illustrating an example of a process of utilizing a third FR molecule that includes a phosphorus-based FR moiety and a CL moiety to form the third non-halogenated FR HALS cross-linker depicted in FIG. 3A, according to one embodiment.

FIG. 8A is a diagram depicting an eighth non-halogenated FR HALS cross-linker of the present disclosure, according to one embodiment.

FIG. 8B is a chemical reaction diagram illustrating an example of a process of utilizing an eighth FR molecule that includes a phosphorus-based FR moiety and a CL moiety to form the eighth non-halogenated FR HALS cross-linker depicted in FIG. 8A, according to one embodiment.

FIG. 9A is a diagram depicting a ninth non-halogenated FR HALS cross-linker of the present disclosure, according to one embodiment.

FIG. 9B is a chemical reaction diagram illustrating an example of a process of utilizing the seventh FR molecule of FIG. 7B to form the ninth non-halogenated FR HALS cross-linker depicted in FIG. 9A, according to one embodiment.

FIG. 16 is a chemical reaction diagram illustrating an example of a process of forming the seventh FR molecule depicted in FIGS. 7B and 9B, according to one embodiment.

FIG. 17 is a chemical reaction diagram illustrating an example of a process of forming the eighth FR molecule depicted in FIG. 8B, according to one embodiment.

DETAILED DESCRIPTION

Figure 2A:
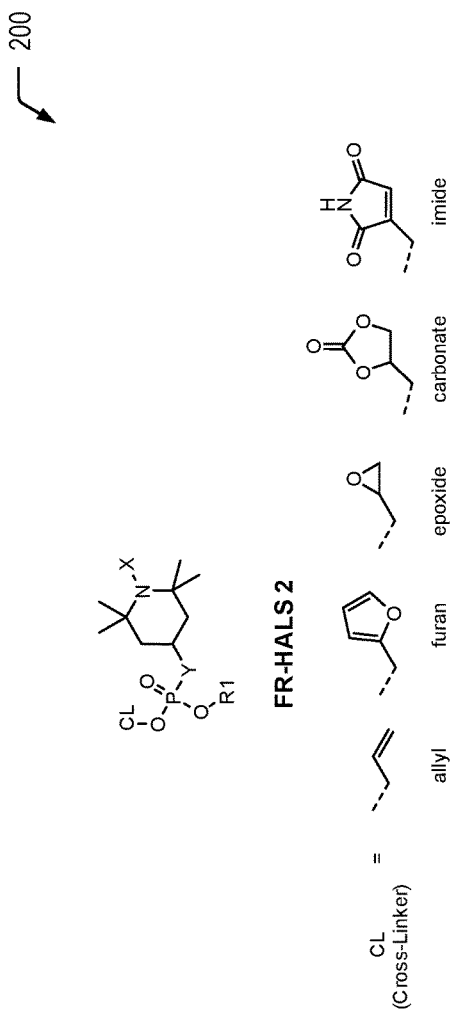
FIG. 2A is a diagram depicting a second non-halogenated FR HALS cross-linker of the present disclosure, according to one embodiment.

The present disclosure describes non-halogenated flame retardant (FR) hindered amine light stabilizer (HALS) cross-linkers and processes for forming non-halogenated FR HALS cross-linkers. The non-halogenated FR HALS molecules of the present disclosure may be formed from a first molecule that includes a hindered amine group and a second molecule that includes a phosphorus-based FR moiety to impart flame retardant characteristics and one or more cross-linkable (CL) moieties. The first molecule may include a derivative of a 2,2,6,6-tetramethylpiperidine (TMP) molecule as a light stabilizer to provide protection against light-induced degradation (e.g., ultraviolet (UV) degradation). By utilizing phosphorus-based materials to impart flame retardancy characteristics, the non-halogenated FR HALS molecules of the present disclosure may reduce or eliminate the loss of light stabilization associated with the release of bromine radicals from conventional brominated flame retardant additives. Further, the CL moiety(s) may enable the non-halogenated FR HALS molecules of the present disclosure to be utilized to form flame retardant, light stabilized, cross-linked polymeric materials.

The non-halogenated FR HALS molecules of the present disclosure include a first portion to impart light stabilization characteristics in order to provide protection against light-induced degradation (e.g., UV degradation). Prior to functionalization, a 2,2,6,6-tetramethylpiperidine (TMP) molecule has the following chemical structure:

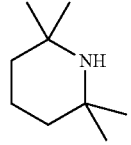

The chemical structure depicted above illustrates that a 2,2,6,6-tetramethylpiperidine molecule is a heterocyclic amine consisting of a six-membered ring and one amine bridge (NH). With respect to nomenclature, the amine bridge in a piperidine molecule represents position 1 of the six-membered ring. The tetramethyl portion of the piperidine prefix indicates that four methyl ($CH_3$) groups are bonded to particular carbon atoms of the five carbon atoms of the six-membered ring. The 2,2 portion of the piperidine prefix indicates that two of the four methyl groups are bonded to the carbon atom at position 2 of the six-membered ring (i.e., adjacent to the amine bridge at position 1). The 6,6 portion of the piperidine prefix indicates that two of the four methyl groups are bonded to the carbon atom at position 6 of the six-membered ring (i.e., adjacent to the amine bridge at position 1). As a result of steric hindrance associated with the four methyl groups adjacent to the amine, the amine is typically referred to as a hindered amine.

In the present disclosure, the first molecule that includes the hindered amine group may correspond to a functionalized derivative of a TMP molecule (with functionalization at positions 1 and 4 of the six-membered ring) having the following formula:

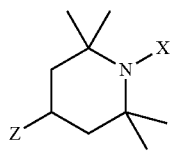

In the above formula, the letter X may represent an oxyl radical (O.), a hydroxyl (OH) group, or an alkyloxy/aryloxy (O—R2) group, with X bonded to the nitrogen atom at position 1 of the six-membered ring. The letter Z may represent a hydroxyl (OH) group, an amine ($NH_2$) group, or an alkyl/aryl amine (NH—R3) group bonded to the carbon atom at position 4 of the six-membered ring. In some cases, the first molecule may correspond to a commercially available TMP derivative, such as a commercially available "TEMPO" derivative (in cases where X=O.) that represents a stable radical. Illustrative, non-limiting examples of commercially available TEMPO derivatives include: 4-hydroxy-2,2,6,6-tetramethylpiperidine 1-oxyl free radical; 4-amino-2,2,6,6-tetramethylpiperidine 1-oxyl free radical; and 4-methylamino-2,2,6,6-tetramethylpiperidine 1-oxyl free radical. Illustrative, non-limiting examples of commercially available amine-functionalized TMP derivatives include: 1-hydroxyl-2,2,6,6-tetramethyl-4-piperidineamine; 1-hydroxyl-2,2,6,6-tetramethyl-4-piperidinol; 1-hydroxyl-N,2,2,6,6-pentaamethyl-4-piperidineamine; and 2,2,6,6-tetramethyl-1-[1-[4-(2-propen-1-yloxy)phenyl]ethoxy]-4-piperidinol. Illustrative, non-limiting examples of commercially available alkyl/aryl amine-functionalized TMP derivatives include: 1-methoxy-2,2,6,6-tetramethyl-4-piperidinol; 1-ethoxy-2,2,6,6-tetramethyl-4-piperidinol; 2,2,6,6-tetramethyl-1-(2-propen-1-loxy)-4-piperidinol; 1-(cyclohexyloxy)-2,2,6,6-tetramethyl-4-piperidinol, 1-(cyclooctyloxy)-2,2,6,6-tetramethyl-4-piperidinol; 1-(2-hydroxy-2-methylpropoxy)-2,2,6,6-tetramethyl-4-piperidinol; 1-methoxy-2,2,6,6-tetramethyl-4-piperidinamine; and 1-ethoxy-2,2,6,6-tetramethyl-4-piperidinamine. In other cases, the first molecule may be synthesized from a commercially available TMP derivative.

The non-halogenated FR HALS molecules of the present disclosure include a second portion that includes a phosphorus-based moiety and CL moiety(s). The phosphorus-based moiety imparts flame retardancy characteristics, and the CL moiety(s) may enable the non-halogenated FR HALS molecules to be utilized as polymeric cross-linkers. In the present disclosure, the second molecule may include a phosphoryl group (i.e., a phosphorus-oxygen double bond) and a chloride group, and the CL moiety(s) may include one or more allyl, furan, epoxide, carbonate, or imide functional groups (among other alternatives).

As described further herein, the cross-linkable, non-halogenated FR HALS molecules of the present disclosure may be formed via addition of the second molecule to the first molecule. For particular CL moieties, such as epoxides, carbonates, and imides (among others), the addition process may be performed after formation of the hindered amine group of the first molecule (e.g., in cases where a piperidine amide bridge of a TMP derivative is to be converted to a nitroxyl radical).

In some cases, the non-halogenated FR HALS molecules of the present disclosure may be utilized as multi-function additives to impart flame retardancy and light stabilization characteristics to a polymeric material, along with characteristics associated with the CL moiety(s). In a particular embodiment, where N—X corresponds to a nitroxyl radical (N—O.), the radical may enable the non-halogenated FR HALS molecules of the present disclosure to be bonded to a variety of polymers or polymeric blends. As an example, the nitroxyl radical may enable a non-halogenated FR HALS molecule of the present disclosure to be chemically bonded to a first polymer chain (at position 1 of the six-membered ring). The one or more CL moieties (linked to the carbon atom at position 4 of the six-membered ring) may further enable the non-halogenated FR HALS molecule to be chemically bonded to one or more additional polymer chains, thereby cross-linking the first polymer chain to the additional polymer chain(s).

Referring to FIG. 1A, a diagram 100 illustrates an example of a first FR-HALS molecule of the present disclosure (identified as "FR-HALS(1)" in FIG. 1A), according to one embodiment. Referring to FIG. 1B, a chemical reaction diagram 110 illustrates an example of a process of forming the first FR-HALS molecule of FIG. 1A.

The top portion of FIG. 1A illustrates that the first FR-HALS molecule has the following chemical formula:

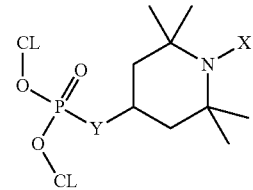

In the formula above depicting the first FR-HALS molecule, X may represent O., OH, or OR2 (where R2 corresponds to an alkyl/aryl group), Y may represent O, NH, or NR3 (where R3 corresponds to an alkyl/aryl group), and CL represents a cross-linkable moiety. The bottom portion of FIG. 1A illustrates examples of functional groups that may correspond to the two CL moieties of the first FR-HALS molecule, such as allyl, furan, epoxide, carbonate, or imide functional groups.

In a particular embodiment, the first FR-HALS molecule depicted in FIG. 1A may be formed according to the process depicted in the chemical reaction diagram 110 of FIG. 1B. FIG. 1B illustrates that a first FR molecule (identified as "FR1" in FIG. 1B) may be utilized to form the first FR-HALS molecule. In some cases, the FR1 molecule may be formed according to the process described further herein with respect to FIG. 10. The FR1 molecule of FIG. 1B represents an example of a chlorophosphate molecule with two CL moieties having the chemical formula (O-CL)$_2$ POCl. In the particular embodiment depicted in FIG. 1B, the first FR-HALS molecule may be formed via addition of the FR1 molecule to a functionalized TMP derivative molecule having the following chemical formula:

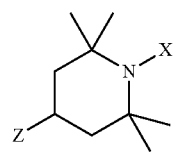

In the above formula, the letter X may represent O., OH, or OR2 (where R2 corresponds to an alkyl/aryl group), and the letter Z may represent OH, NH$_2$, or NHR3 (where R3 corresponds to an alkyl/aryl group).

As an example, the addition reaction may include chemically reacting the functionalized TMP derivative molecule with the FR1 molecule. As a prophetic example, triethylamine (1.2 equiv.) and N,N-dimethylaminopyridine (DMAP) (3.0 mol %) may be added to a stirred solution of the functionalized TMP derivative molecule (1.0 equiv.) in 150 mL of DCM, under argon, and cooled to 0° C. A solution of FR1 in DCM (1.1 equiv.) may be added dropwise at 0° C. Upon completion of the addition, the reaction mixture may be allowed to stir for 1 hour at 0° C., and may be warmed to room temperature or reflux and stirred for 16 hours. The reaction mixture may be subsequently washed twice with water, followed by 1N HCl, three additional washes of water, and brine. The organic layer may be dried over anhydrous sodium sulfate, filtered, and the solvents removed in vacuo. The product may be purified by fractional distillation.

Thus, FIGS. 1A and 1B illustrate an example of a first non-halogenated FR HALS molecule of the present disclosure and a process for forming the first non-halogenated FR HALS molecule. The first portion of the first non-halogenated FR HALS molecule corresponding to the TMP derivative may provide protection against light-induced degradation (e.g., UV degradation). The second portion of the first non-halogenated FR HALS molecule corresponding to the first FR molecule imparts flame retardancy characteristics via the phosphorus-based moiety, and the two CL moieties may enable the first non-halogenated FR HALS molecule to be utilized as a polymeric cross-linker.

Figure 2B:
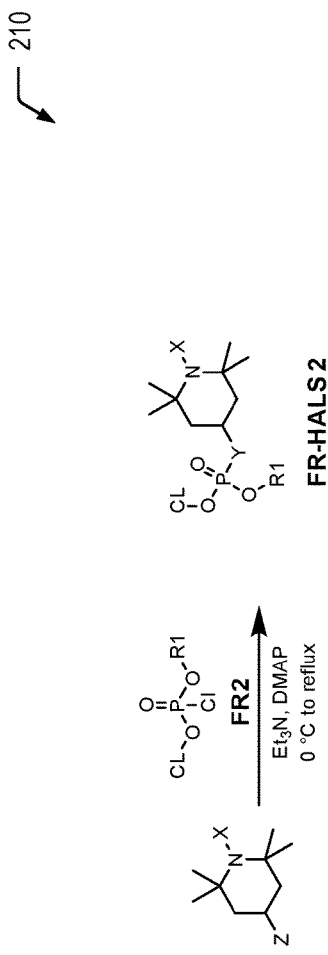
FIG. 2B is a chemical reaction diagram illustrating an example of a process of utilizing a second FR molecule that includes a phosphorus-based FR moiety and a CL moiety to form the second non-halogenated FR HALS cross-linker depicted in FIG. 2A, according to one embodiment.

Referring to FIG. 2A, a diagram 200 illustrates an example of a second FR-HALS molecule of the present disclosure (identified as "FR-HALS(2)" in FIG. 2A), according to one embodiment. Referring to FIG. 2B, a chemical reaction diagram 210 illustrates an example of a process of forming the second FR-HALS molecule of FIG. 2A.

The top portion of FIG. 2A illustrates that the second FR-HALS molecule has the following chemical formula:

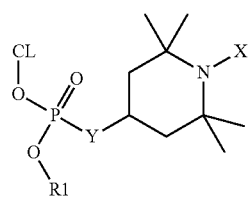

In the formula above depicting the second FR-HALS molecule, R1 may represent an alkyl/aryl group, X may represent O., OH, or OR2 (where R2 corresponds to an alkyl/aryl group), Y may represent O, NH, or NR3 (where R3 corresponds to an alkyl/aryl group), and CL represents a cross-linkable moiety. The bottom portion of FIG. 2A illustrates examples of functional groups that may correspond to the single CL moiety of the second FR-HALS molecule, such as an allyl, furan, epoxide, carbonate, or imide functional group.

In a particular embodiment, the second FR-HALS molecule depicted in FIG. 2A may be formed according to the process depicted in the chemical reaction diagram 210 of FIG. 2B. FIG. 2B illustrates that a second FR molecule (identified as "FR2" in FIG. 2B) may be utilized to form the second FR-HALS molecule. In some cases, the FR2 molecule may be formed according to one of the processes described further herein with respect to FIG. 11. The FR2 molecule of FIG. 2B represents an example of a chlorophosphate molecule with one CL moiety having the chemical formula OR1(O-CL)POCl, where R1 corresponds to an alkyl/aryl group. In the particular embodiment depicted in FIG. 2B, the second FR-HALS molecule may be formed via addition of the FR2 molecule to a functionalized TMP derivative molecule having the following chemical formula:

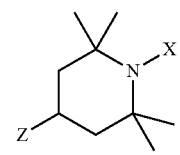

As previously described herein, in the above formula, the letter X may represent O., OH, or OR2 (where R2 corresponds to an alkyl/aryl group), and the letter Z may represent OH, NH$_2$, or NHR3 (where R3 corresponds to an alkyl/aryl group).

As an example, the addition reaction may include chemically reacting the functionalized TMP derivative molecule with the FR2 molecule. In a particular embodiment, the addition reaction may be performed in a manner similar to that described previously herein with respect to FIG. 1B.

Thus, FIGS. 2A and 2B illustrate an example of a second non-halogenated FR HALS molecule of the present disclosure and a process for forming the second non-halogenated FR HALS molecule. The first portion of the second non-halogenated FR HALS molecule corresponding to the TMP derivative may provide protection against light-induced degradation (e.g., UV degradation). The second portion of the second non-halogenated FR HALS molecule corresponding to the FR2 molecule imparts flame retardancy characteristics via the phosphorus-based moiety, and the CL moiety may enable the second non-halogenated FR HALS molecule to be utilized as a polymeric cross-linker.

Referring to FIG. 3A, a diagram 300 illustrates an example of a third FR-HALS molecule of the present disclosure (identified as "FR-HALS(3)" in FIG. 3A), according to one embodiment. Referring to FIG. 3B, a chemical reaction diagram 310 illustrates an example of a process of forming the third FR-HALS molecule of FIG. 3A.

The top portion of FIG. 3A illustrates that the third FR-HALS molecule has the following chemical formula:

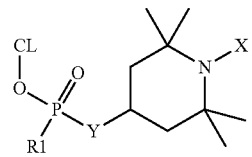

In the formula above depicting the third FR-HALS molecule, R1 may represent an alkyl/aryl group, X may represent O., OH, or OR2 (where R2 corresponds to an alkyl/aryl group), Y may represent O, NH, or NR3 (where R3 corresponds to an alkyl/aryl group), and CL represents a cross-linkable moiety. The bottom portion of FIG. 3A illustrates examples of functional groups that may correspond to the single CL moiety of the third FR-HALS molecule, such as an allyl, furan, epoxide, carbonate, or imide functional group.

In a particular embodiment, the third FR-HALS molecule depicted in FIG. 3A may be formed according to the process depicted in the chemical reaction diagram 310 of FIG. 3B. FIG. 3B illustrates that a third FR molecule (identified as "FR3" in FIG. 3B) may be utilized to form the third FR-HALS molecule. In some cases, the FR3 molecule may be formed according to the process described further herein with respect to FIG. 12. The FR3 molecule of FIG. 3B represents an example of a chlorophosphinate molecule with one CL moiety having the chemical formula R1(O-CL) POCl, where R1 corresponds to an alkyl/aryl group. In the particular embodiment depicted in FIG. 3B, the third FR-HALS molecule may be formed via addition of the FR3 molecule to a functionalized TMP derivative molecule having the following chemical formula:

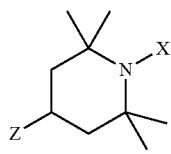

As previously described herein, in the above formula, the letter X may represent O., OH, or OR2 (where R2 corresponds to an alkyl/aryl group), and the letter Z may represent OH, $NH_2$, or NHR3 (where R3 corresponds to an alkyl/aryl group).

As an example, the addition reaction may include chemically reacting the functionalized TMP derivative molecule with the FR3 molecule. In a particular embodiment, the addition reaction may be performed in a manner similar to that described previously herein with respect to FIG. 1B.

Thus, FIGS. 3A and 3B illustrate an example of a third non-halogenated FR HALS molecule of the present disclosure and a process for forming the third non-halogenated FR HALS molecule. The first portion of the third non-halogenated FR HALS molecule corresponding to the TMP derivative may provide protection against light-induced degradation (e.g., UV degradation). The second portion of the third non-halogenated FR HALS molecule corresponding to the FR3 molecule imparts flame retardancy characteristics via the phosphorus-based moiety, and the CL moiety may enable the third non-halogenated FR HALS molecule to be utilized as a polymeric cross-linker.

Figure 4A:
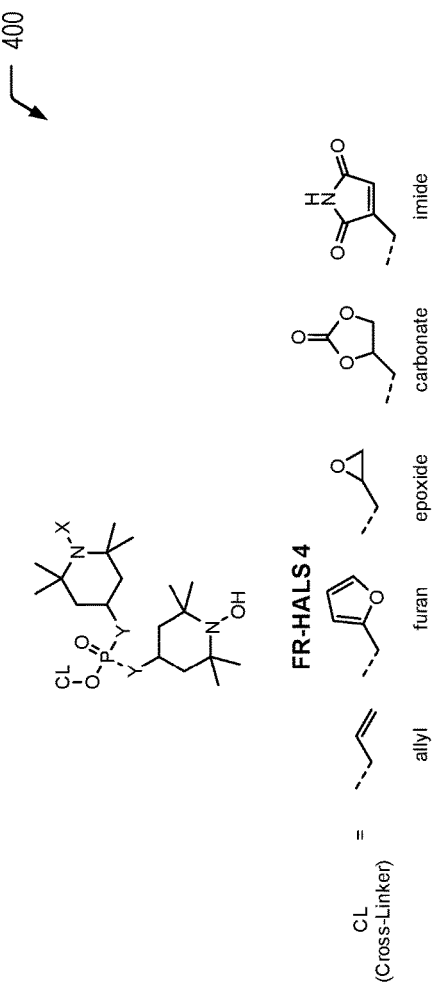
FIG. 4A is a diagram depicting a fourth non-halogenated FR HALS cross-linker of the present disclosure, according to one embodiment.
Figure 4B:
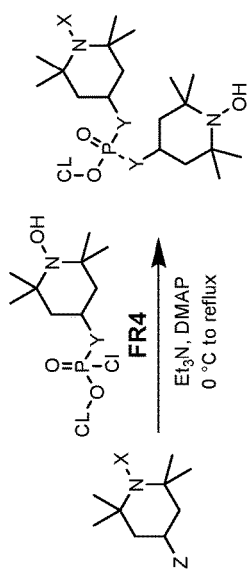
FIG. 4B is a chemical reaction diagram illustrating an example of a process of utilizing a fourth FR molecule that includes a phosphorus-based FR moiety and a CL moiety to form the fourth non-halogenated FR HALS cross-linker depicted in FIG. 4A, according to one embodiment.

Referring to FIG. 4A, a diagram 400 illustrates an example of a fourth FR-HALS molecule of the present disclosure (identified as "FR-HALS(4)" in FIG. 4A), according to one embodiment. Referring to FIG. 4B, a chemical reaction diagram 410 illustrates an example of a process of forming the fourth FR-HALS molecule of FIG. 4A.

The top portion of FIG. 4A illustrates that the fourth FR-HALS molecule has the following chemical formula:

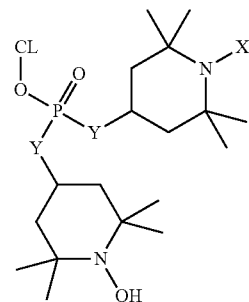

In the formula above depicting the fourth FR-HALS molecule, X may represent O., OH, or OR2 (where R2 corresponds to an alkyl/aryl group), Y may represent O, NH, or NR3 (where R3 corresponds to an alkyl/aryl group), and CL represents a cross-linkable moiety. The bottom portion of FIG. 4A illustrates examples of functional groups that may correspond to the single CL moiety of the fourth FR-HALS molecule, such as an allyl, furan, epoxide, carbonate, or imide functional group.

In a particular embodiment, the fourth FR-HALS molecule depicted in FIG. 4A may be formed according to the process depicted in the chemical reaction diagram 410 of FIG. 4B. FIG. 4B illustrates that a fourth FR molecule (identified as "FR4" in FIG. 4B) may be utilized to form the fourth FR-HALS molecule. In some cases, the FR4 molecule may be formed according to the process described further herein with respect to FIG. 13. The FR4 molecule of FIG. 4B represents an example of a chlorophosphate molecule with one CL moiety and a 1-hydroxy functionalized TMP derivative bonded to an oxygen atom at position 4 of the piperidine ring. In the particular embodiment depicted in FIG. 4B, the fourth FR-HALS molecule may be formed via addition of the FR4 molecule to a functionalized TMP derivative molecule having the following chemical formula:

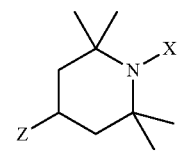

As previously described herein, in the above formula, the letter X may represent O., OH, or OR2 (where R2 corresponds to an alkyl/aryl group), and the letter Z may represent OH, $NH_2$, or NHR3 (where R3 corresponds to an alkyl/aryl group).

As an example, the addition reaction may include chemically reacting the functionalized TMP derivative molecule with the FR4 molecule. In a particular embodiment, the addition reaction may be performed in a manner similar to that described previously herein with respect to FIG. 1B.

Thus, FIGS. 4A and 4B illustrate an example of a fourth non-halogenated FR HALS molecule of the present disclosure and a process for forming the fourth non-halogenated FR HALS molecule. The first portion of the fourth non-halogenated FR HALS molecule corresponding to the TMP derivative may provide protection against light-induced degradation (e.g., UV degradation). The second portion of the fourth non-halogenated FR HALS molecule corresponding to the FR4 molecule imparts flame retardancy characteristics via the phosphorus-based moiety, and the CL moiety may enable the fourth non-halogenated FR HALS molecule to be utilized as a polymeric cross-linker. Further, the hydroxyl-functionalized TMP derivative of the FR4 molecule may impart additional protection against light-induced degradation.

Figures 5A, 5B:
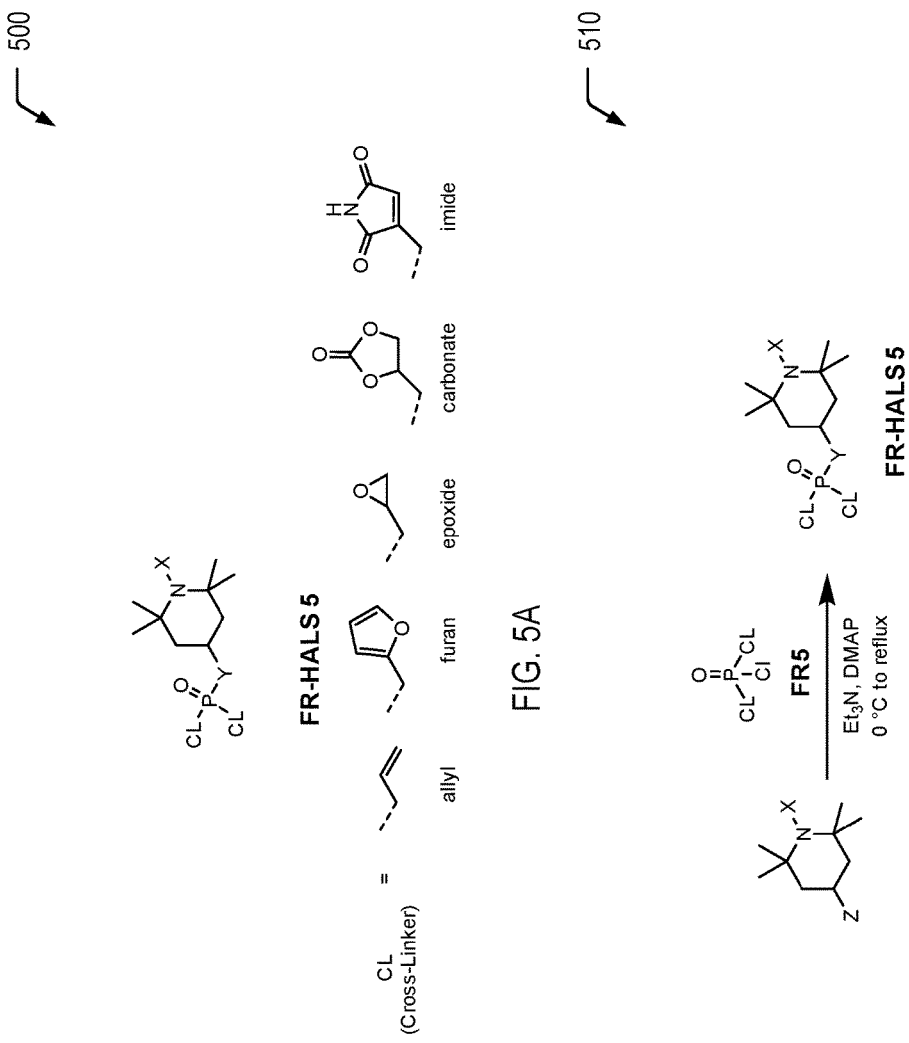
FIG. 5A is a diagram depicting a fifth non-halogenated FR HALS cross-linker of the present disclosure, according to one embodiment.
FIG. 5B is a chemical reaction diagram illustrating an example of a process of utilizing a fifth FR molecule that includes a phosphorus-based FR moiety and CL moieties to form the fifth non-halogenated FR HALS cross-linker depicted in FIG. 5A, according to one embodiment.

Referring to FIG. 5A, a diagram 500 illustrates an example of a fifth FR-HALS molecule of the present disclosure (identified as "FR-HALS(5)" in FIG. 5A), according to one embodiment. Referring to FIG. 5B, a chemical reaction diagram 510 illustrates an example of a process of forming the fifth FR-HALS molecule of FIG. 5A.

The top portion of FIG. 5A illustrates that the fifth FR-HALS molecule has the following chemical formula:

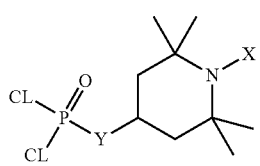

In the formula above depicting the fifth FR-HALS molecule, X may represent O., OH, or OR2 (where R2 corresponds to an alkyl/aryl group), Y may represent O, NH, or NR3 (where R3 corresponds to an alkyl/aryl group), and CL represents the cross-linkable moieties. The bottom portion of FIG. 5A illustrates examples of functional groups that may correspond to the two CL moieties of the fifth FR-HALS molecule, such as allyl, furan, epoxide, carbonate, or imide functional groups.

In a particular embodiment, the fifth FR-HALS molecule depicted in FIG. 5A may be formed according to the process depicted in the chemical reaction diagram 510 of FIG. 5B. FIG. 5B illustrates that a fifth FR molecule (identified as "FR5" in FIG. 5B) may be utilized to form the fifth FR-HALS molecule. In some cases, the FR5 molecule may be formed according to one of the processes described further herein with respect to FIG. 14. The FR5 molecule of FIG. 5B represents an example of a chlorophosphine oxide molecule with two CL moieties having the chemical formula $(CL)_2POCl$. In the particular embodiment depicted in FIG. 5B, the fifth FR-HALS molecule may be formed via addition of the FR5 molecule to a functionalized TMP derivative molecule having the following chemical formula:

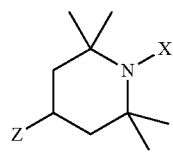

As previously described herein, in the above formula, the letter X may represent O., OH, or OR2 (where R2 corresponds to an alkyl/aryl group), and the letter Z may represent OH, $NH_2$, or NHR3 (where R3 corresponds to an alkyl/aryl group).

As an example, the addition reaction may include chemically reacting the functionalized TMP derivative molecule with the FR5 molecule. In a particular embodiment, the addition reaction may be performed in a manner similar to that described previously herein with respect to FIG. 1B.

Thus, FIGS. 5A and 5B illustrate an example of a fifth non-halogenated FR HALS molecule of the present disclosure and a process for forming the fifth non-halogenated FR HALS molecule. The first portion of the fifth non-halogenated FR HALS molecule corresponding to the TMP derivative may provide protection against light-induced degradation (e.g., UV degradation). The second portion of the fifth non-halogenated FR HALS molecule corresponding to the FR5 molecule imparts flame retardancy characteristics via the phosphorus-based moiety, and the two CL moieties may enable the fifth non-halogenated FR HALS molecule to be utilized as a polymeric cross-linker.

Figures 6A, 6B:
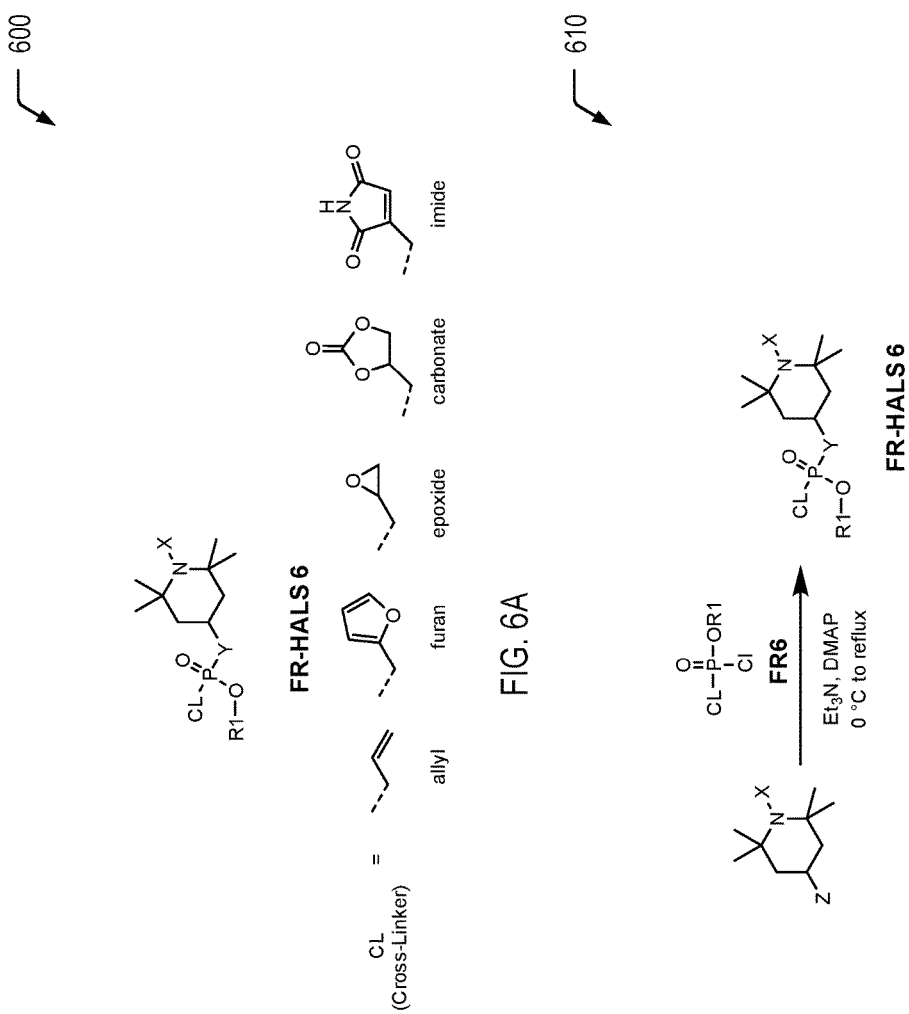
FIG. 6A is a diagram depicting a sixth non-halogenated FR HALS cross-linker of the present disclosure, according to one embodiment.
FIG. 6B is a chemical reaction diagram illustrating an example of a process of utilizing a sixth FR molecule that includes a phosphorus-based FR moiety and a CL moiety to form the sixth non-halogenated FR HALS cross-linker depicted in FIG. 6A, according to one embodiment.

Referring to FIG. 6A, a diagram 600 illustrates an example of a sixth FR-HALS molecule of the present disclosure (identified as "FR-HALS(6)" in FIG. 6A), according to one embodiment. Referring to FIG. 6B, a chemical reaction diagram 610 illustrates an example of a process of forming the sixth FR-HALS molecule of FIG. 6A.

The top portion of FIG. 6A illustrates that the sixth FR-HALS molecule has the following chemical formula:

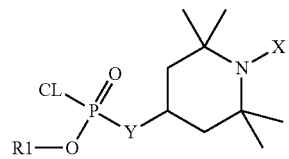

In the formula above depicting the third FR-HALS molecule, R1 may represent an alkyl/aryl group, X may represent O., OH, or OR2 (where R2 corresponds to an alkyl/aryl group), Y may represent O, NH, or NR3 (where R3 corresponds to an alkyl/aryl group), and CL represents a cross-linkable moiety. The bottom portion of FIG. 6A illustrates examples of functional groups that may correspond to the single CL moiety of the sixth FR-HALS molecule, such as an allyl, furan, epoxide, carbonate, or imide functional group.

In a particular embodiment, the sixth FR-HALS molecule depicted in FIG. 6A may be formed according to the process depicted in the chemical reaction diagram 610 of FIG. 6B. FIG. 6B illustrates that a sixth FR molecule (identified as "FR6" in FIG. 6B) may be utilized to form the sixth FR-HALS molecule. In some cases, the FR6 molecule may be formed according to one of the processes described further herein with respect to FIG. 15. The FR6 molecule of FIG. 6B represents an example of a chlorophosphinate molecule with one CL moiety having the chemical formula OR1(CL)POCl, where R1 corresponds to an alkyl/aryl group. In the particular embodiment depicted in FIG. 6B, the sixth FR-HALS molecule may be formed via addition of the FR6 molecule to a functionalized TMP derivative molecule having the following chemical formula:

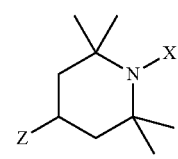

As previously described herein, in the above formula, the letter X may represent O., OH, or OR2 (where R2 corresponds to an alkyl/aryl group), and the letter Z may represent OH, $NH_2$, or NHR3 (where R3 corresponds to an alkyl/aryl group).

As an example, the addition reaction may include chemically reacting the functionalized TMP derivative molecule with the FR6 molecule. In a particular embodiment, the addition reaction may be performed in a manner similar to that described previously herein with respect to FIG. 1B.

Thus, FIGS. 6A and 6B illustrate an example of a sixth non-halogenated FR HALS molecule of the present disclosure and a process for forming the sixth non-halogenated FR HALS molecule. The first portion of the sixth non-halogenated FR HALS molecule corresponding to the TMP derivative may provide protection against light-induced degradation (e.g., UV degradation). The second portion of the sixth non-halogenated FR HALS molecule corresponding to the FR6 molecule imparts flame retardancy characteristics via the phosphorus-based moiety, and the CL moiety may enable the sixth non-halogenated FR HALS molecule to be utilized as a polymeric cross-linker.

Figure 7A:
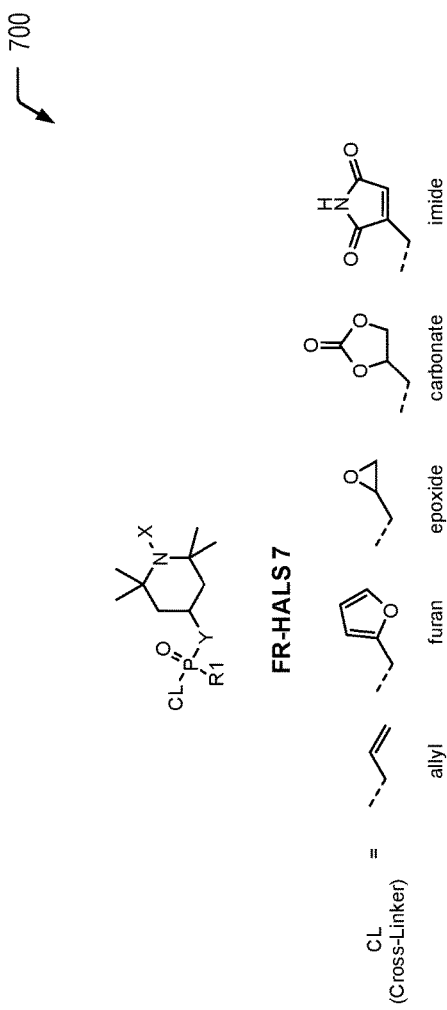
FIG. 7A is a diagram depicting a seventh non-halogenated FR HALS cross-linker of the present disclosure, according to one embodiment.
Figure 7B:
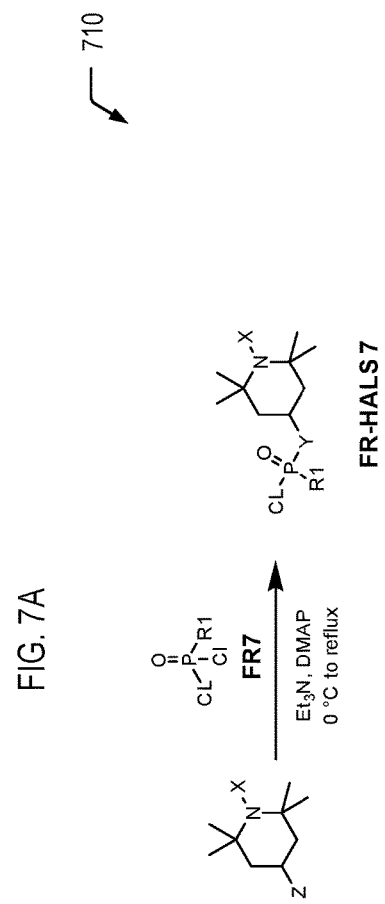
FIG. 7B is a chemical reaction diagram illustrating an example of a process of utilizing a seventh FR molecule that includes a phosphorus-based FR moiety and a CL moiety to form the seventh non-halogenated FR HALS cross-linker depicted in FIG. 7A, according to one embodiment.

Referring to FIG. 7A, a diagram 700 illustrates an example of a seventh FR-HALS molecule of the present disclosure (identified as "FR-HALS(7)" in FIG. 7A), according to one embodiment. Referring to FIG. 7B, a chemical reaction diagram 710 illustrates an example of a process of forming the seventh FR-HALS molecule of FIG. 7A.

The top portion of FIG. 7A illustrates that the seventh FR-HALS molecule has the following chemical formula:

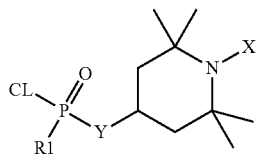

In the formula above depicting the seventh FR-HALS molecule, R1 may represent an alkyl/aryl group, X may represent O., OH, or OR2 (where R2 corresponds to an alkyl/aryl group), Y may represent O, NH, or NR3 (where R3 corresponds to an alkyl/aryl group), and CL represents a cross-linkable moiety. The bottom portion of FIG. 7A illustrates examples of functional groups that may correspond to the single CL moiety of the seventh FR-HALS molecule, such as an allyl, furan, epoxide, carbonate, or imide functional group.

In a particular embodiment, the seventh FR-HALS molecule depicted in FIG. 7A may be formed according to the process depicted in the chemical reaction diagram 710 of FIG. 7B. FIG. 7B illustrates that a seventh FR molecule (identified as "FR7" in FIG. 7B) may be utilized to form the seventh FR-HALS molecule. In some cases, the FR7 molecule may be formed according to the process described further herein with respect to FIG. 16. The FR7 molecule of FIG. 7B represents an example of a chlorophosphine oxide molecule with one CL moiety having the chemical formula R1(CL)POCl, where R1 corresponds to an alkyl/aryl group. In the particular embodiment depicted in FIG. 7B, the seventh FR-HALS molecule may be formed via addition of the FR7 molecule to a functionalized TMP derivative molecule having the following chemical formula:

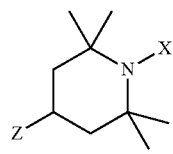

As previously described herein, in the above formula, the letter X may represent O., OH, or OR2 (where R2 corresponds to an alkyl/aryl group), and the letter Z may represent OH, NH$_2$, or NHR3 (where R3 corresponds to an alkyl/aryl group).

As an example, the addition reaction may include chemically reacting the functionalized TMP derivative molecule with the FR7 molecule. In a particular embodiment, the addition reaction may be performed in a manner similar to that described previously herein with respect to FIG. 1B.

Thus, FIGS. 7A and 7B illustrate an example of a seventh non-halogenated FR HALS molecule of the present disclosure and a process for forming the seventh non-halogenated FR HALS molecule. The first portion of the seventh non-halogenated FR HALS molecule corresponding to the TMP derivative may provide protection against light-induced degradation (e.g., UV degradation). The second portion of the seventh non-halogenated FR HALS molecule corresponding to the FR7 molecule imparts flame retardancy characteristics via the phosphorus-based moiety, and the CL moiety may enable the seventh non-halogenated FR HALS molecule to be utilized as a polymeric cross-linker.

Referring to FIG. 8A, a diagram 800 illustrates an example of an eighth FR-HALS molecule of the present disclosure (identified as "FR-HALS(8)" in FIG. 8A), according to one embodiment. Referring to FIG. 8B, a chemical reaction diagram 810 illustrates an example of a process of forming the eighth FR-HALS molecule of FIG. 8A.

The top portion of FIG. 8A illustrates that the eighth FR-HALS molecule has the following chemical formula:

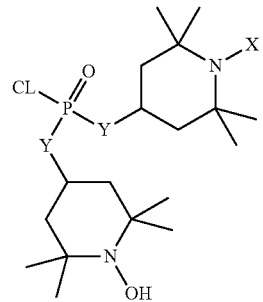

In the formula above depicting the eighth FR-HALS molecule, X may represent O., OH, or OR2 (where R2 corresponds to an alkyl/aryl group), Y may represent O, NH, or NR3 (where R3 corresponds to an alkyl/aryl group), and CL represents a cross-linkable moiety. The bottom portion of FIG. 8A illustrates examples of functional groups that may correspond to the single CL moiety of the eighth FR-HALS molecule, such as an allyl, furan, epoxide, carbonate, or imide functional group.

In a particular embodiment, the eighth FR-HALS molecule depicted in FIG. 8A may be formed according to the process depicted in the chemical reaction diagram 810 of FIG. 8B. FIG. 8B illustrates that an eighth FR molecule (identified as "FR8" in FIG. 8B) may be utilized to form the eighth FR-HALS molecule. In some cases, the FR8 molecule may be formed according to the process described further herein with respect to FIG. 17. The FR8 molecule of FIG. 8B represents an example of a chlorophosphinate molecule with one CL moiety and a TMP derivative with a hydroxyl group bonded to the nitrogen atom at position 1 of the six-membered ring and an oxygen atom of the chlorophosphinate molecule bonded to the carbon atom at position 4 of the six-membered ring. In the particular embodiment depicted in FIG. 8B, the eighth FR-HALS molecule may be formed via addition of the FR8 molecule to a functionalized TMP derivative molecule having the following chemical formula:

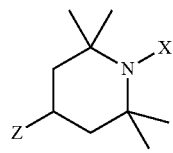

As previously described herein, in the above formula, the letter X may represent O., OH, or OR2 (where R2 corresponds to an alkyl/aryl group), and the letter Z may represent OH, $NH_2$, or NHR3 (where R3 corresponds to an alkyl/aryl group).

As an example, the addition reaction may include chemically reacting the functionalized TMP derivative molecule with the FR8 molecule. In a particular embodiment, the addition reaction may be performed in a manner similar to that described previously herein with respect to FIG. 1B.

Thus, FIGS. 8A and 8B illustrate an example of an eighth non-halogenated FR HALS molecule of the present disclosure and a process for forming the eighth non-halogenated FR HALS molecule. The first portion of the eighth non-halogenated FR HALS molecule corresponding to the TMP derivative may provide protection against light-induced degradation (e.g., UV degradation). The second portion of the eighth non-halogenated FR HALS molecule corresponding to the FR8 molecule imparts flame retardancy characteristics via the phosphorus-based moiety, and the CL moiety may enable the eighth non-halogenated FR HALS molecule to be utilized as a polymeric cross-linker. Further, the additional hindered amine of the FR8 molecule may impart additional protection against light-induced degradation.

Referring to FIG. 9A, a diagram 900 illustrates an example of a ninth FR-HAL S molecule of the present disclosure (identified as "FR-HALS(9)" in FIG. 9A), according to one embodiment. Referring to FIG. 9B, a chemical reaction diagram 910 illustrates an example of a process of forming the ninth FR-HALS molecule of FIG. 9A.

The top portion of FIG. 9A illustrates that the ninth FR-HALS molecule has the following chemical formula:

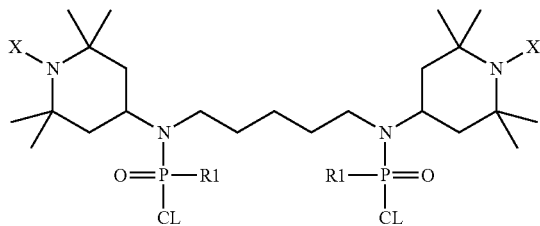

In the formula above depicting the ninth FR-HALS molecule, R1 may represent an alkyl/aryl group, X may represent O., OH, or OR2 (where R2 corresponds to an alkyl/aryl group), and CL represents a cross-linkable moiety. The bottom portion of FIG. 9A illustrates examples of functional groups that may correspond to the CL moieties of the ninth FR-HALS molecule, such as allyl, furan, epoxide, carbonate, or imide functional groups.

In a particular embodiment, the ninth FR-HALS molecule depicted in FIG. 9A may be formed according to the process depicted in the chemical reaction diagram 910 of FIG. 9B. FIG. 9B illustrates that the FR7 molecule of FIG. 7B may be utilized to form the ninth FR-HALS molecule. In the particular embodiment depicted in FIG. 9B, the ninth FR-HALS molecule may be formed via a chemical reaction of the FR7 molecule with a molecule that includes two functionalized TMP molecules bonded via amide linkages, represented by the following chemical formula:

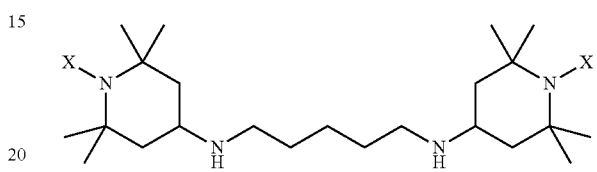

As previously described herein, in the above formula, the letter X may represent O., OH, or OR2 (where R2 corresponds to an alkyl/aryl group). As an example, the chemical reaction may include chemically reacting the above molecule with the FR7 molecule. In a particular embodiment, the reaction may be performed in a manner similar to that described previously herein with respect to FIG. 7B.

Thus, FIGS. 9A and 9B illustrate an example of a ninth non-halogenated FR HALS molecule of the present disclosure and a process for forming the ninth non-halogenated FR HALS molecule. The first portion of the ninth non-halogenated FR HALS molecule corresponding to the TMP derivative (including two functionalized TMP derivatives bonded via amide linkages) may provide protection against light-induced degradation (e.g., UV degradation). The second portion of the ninth non-halogenated FR HALS molecule corresponding to the FR7 molecule imparts flame retardancy characteristics via the phosphorus-based moiety, and the CL moiety may enable the ninth non-halogenated FR HALS molecule to be utilized as a polymeric cross-linker. Further, the additional hindered amine of the ninth non-halogenated FR HALS molecule may impart additional protection against light-induced degradation.

Figures 10, 11:
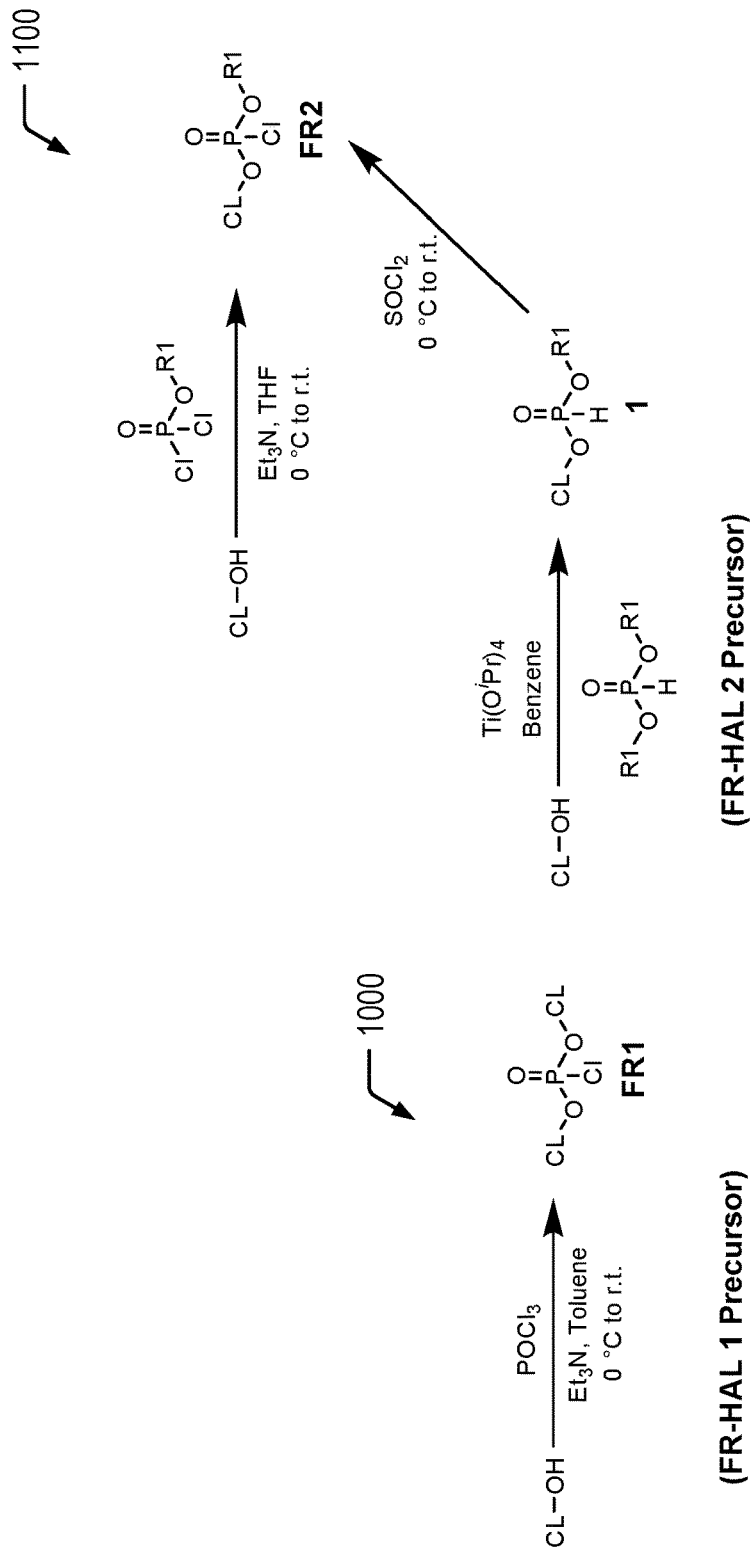
FIG. 10 is a chemical reaction diagram illustrating an example of a process of forming the first FR molecule depicted in FIG. 1B, according to one embodiment.
FIG. 11 is a chemical reaction diagram illustrating examples of alternative processes of forming the second FR molecule depicted in FIG. 2B, according to one embodiment.

Referring to FIG. 10, a chemical reaction diagram 1000 illustrates an example of a process of forming the FR1 molecule depicted in FIG. 1B, according to one embodiment. The FR1 molecule represents an example of a molecule that includes a phosphoryl group (i.e., a phosphorus-oxygen double bond), a chloride group, and two CL moieties. As illustrated in FIG. 1B, the chloride group may react with a functional group (represented as Y) of the functionalized TMP derivative molecule depicted on the left side of the chemical reaction diagram 110 to form the first FR-HALS molecule depicted on the right side of the chemical reaction diagram 110. As illustrated and previously described herein with respect to FIG. 1A, the CL moieties may include allyl, furan, epoxide, carbonate, or imide functional groups (among other alternatives).

FIG. 10 illustrates that an alcohol containing one of the CL moieties (identified as "CL-OH" in FIG. 10) and phosphoryl chloride ($POCl_3$) may be utilized to form the FR1 molecule. As a prophetic example, to a stirred solution of $POCl_3$ (1.0 equiv) in toluene at 0° C. may be added a mixture of CL-functionalized hydroxyl moiety (1.8 equiv) and $Et_3N$ (1.8 equiv). After stirring overnight, $Et_3N \cdot HCl$ may be removed as a solid by filtration. The filtrate containing the FR1 product in toluene may be concentrated in vacuo, and purified by fractional distillation.

Referring to FIG. 11, a chemical reaction diagram 1100 illustrates examples of alternative processes of forming the FR2 molecule depicted in FIG. 2B, according to one embodiment. The FR2 molecule represents an example of a molecule that includes a phosphoryl group (i.e., a phosphorus-oxygen double bond), a chloride group, an alkoxy/aryloxy group (O—R1), and one CL moiety. As illustrated in FIG. 2B, the chloride group may react with a functional group (represented as Y) of the functionalized TMP derivative molecule depicted on the left side of the chemical reaction diagram 210 to form the second FR-HALS molecule depicted on the right side of the chemical reaction diagram 210. As illustrated and previously described herein with respect to FIG. 2A, the CL moiety may include an allyl, furan, epoxide, carbonate, or imide functional group (among other alternatives).

In the first chemical reaction depicted at the top of FIG. 11, the FR2 molecule is formed via a one-step process via reaction of an alcohol containing one of the CL moieties (identified as "CL-OH" in FIG. 11) with a dichlorophosphate molecule via careful addition and stoichiometric control.

As an illustrative, non-limiting example, the alcohol (CL-OH) may correspond to allyl alcohol when the CL moiety corresponds to an allyl group, and the dichlorophosphate molecule may correspond to phenyl dichlorophosphate (i.e., where R1 represents a phenyl group). As a prophetic example, to a stirred solution that includes allyl alcohol (1.0 eq.) and triethylamine (2.0 eq.) in anhydrous THF, phenyl dichlorophosphate (1.3 eq.) may be added dropwise at 0° C., and the reaction mixture may be stirred at ambient temperature for 2 hours or the reaction mixture may be heated up to reflux (60-65° C.) for an extended reaction time (4 hours). The reaction mixture may be cooled to ambient temperature and filtered to remove the triethylamine hydrochloride salt. The solvents of the filtrate may be removed in vacuo, and the product may be purified by fractional distillation.

FIG. 11 further illustrates an alternative process of forming the FR2 molecule. The first chemical reaction illustrates that an alcohol containing one of the CL moieties (identified as "CL-OH" in FIG. 11) may be reacted with titanium (IV) isopropoxide and a phosphonic acid di-ester via a pseudo-esterification to form an intermediate molecule. The second chemical reaction illustrates that the intermediate molecule may be reacted with thionyl chloride to form the FR2 molecule.

As an illustrative, non-limiting example, the alcohol (CL-OH) may correspond to allyl alcohol when the CL moiety corresponds to an allyl group, and the phosphonic acid di-ester may correspond to phosphonic acid diphenyl ester (i.e., where R1 represents a phenyl group). As a prophetic example, diaryl phosphite (5.5 mmol) may be added to a solution of titanium (IV) isopropoxide, $Ti(OPr)_4$ (11 mmol), in allyl alcohol (excess). This solution may be diluted with benzene. The reaction mixture may be heated to 40° C. until completion. The mixture may be poured into water, extracted with $CH_2Cl_2$ (3×), dried over $MgSO_4$, and solvent and volatile components may be removed in vacuo. The products may be purified by fractional distillation or recrystallization. The product from the first step (1.0 eq.), in dry acetonitrile (MeCN), toluene, or dichloromethane (DCM), may be added to a solution of trichloroisocyanuric acid (0.33 eq.), N-chlorosuccinimide (1.0 eq.), or tert-butyl hypochlorite (1.0 eq.) in the same solvent at room temperature, under an $N_2$ atmosphere. Upon formation of a precipitate, the reaction may be stirred at room temperature for an additional 2 hours. Upon completion of the reaction, as determined by $^{31}P$ NMR, the reaction mixture may be passed through a 0.45 μm Whatman syringe filter and concentrated under vacuum. Next, thionyl chloride ($SOCl_2$) may be dissolved in a suitable solvent, such as carbon tetrachloride ($CCl_4$), and the chemical reaction may be performed from 0° C. to room temperature.

Figure 12:
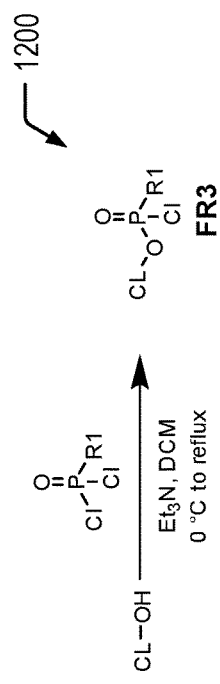
FIG. 12 is a chemical reaction diagram illustrating an example of a process of forming the third FR molecule depicted in FIG. 3B, according to one embodiment.

Referring to FIG. 12, a chemical reaction diagram 1200 illustrates an example of a process of forming the FR3 molecule depicted in FIG. 3B, according to one embodiment. The FR3 molecule represents an example of a molecule that includes a phosphoryl group (i.e., a phosphorus-oxygen double bond), a chloride group, an alkyl/aryl group (R1), and one CL moiety. As illustrated in FIG. 3B, the chloride group may react with a functional group (represented as Y) of the functionalized TMP derivative molecule depicted on the left side of the chemical reaction diagram 310 to form the third FR-HALS molecule depicted on the right side of the chemical reaction diagram 310. As illustrated and previously described herein with respect to FIG. 3A, the CL moiety may include an allyl, furan, epoxide, carbonate, or imide functional group (among other alternatives).

FIG. 12 illustrates that an alcohol containing one of the CL moieties (identified as "CL-OH" in FIG. 10) and phosphoryl chloride ($POCl_3$) may be utilized to form the FR3 molecule. As a prophetic example, CL-OH (1 equiv.) which may be dissolved in diethyl ether, THF, or DCM may be slowly added to a mixture of alkyl- or aryl-phosphonic dichloride (1 equiv.) and triethylamine (1.1 equiv.) in ether, THF, or DCM at 0-5° C. under nitrogen atmosphere. The reaction may be heated to reflux for 6 hours or more. Triethylamine hydrochloride may be filtered and the filtrate may be concentrated in vacuo, and purified by fractional distillation.

Figure 13:
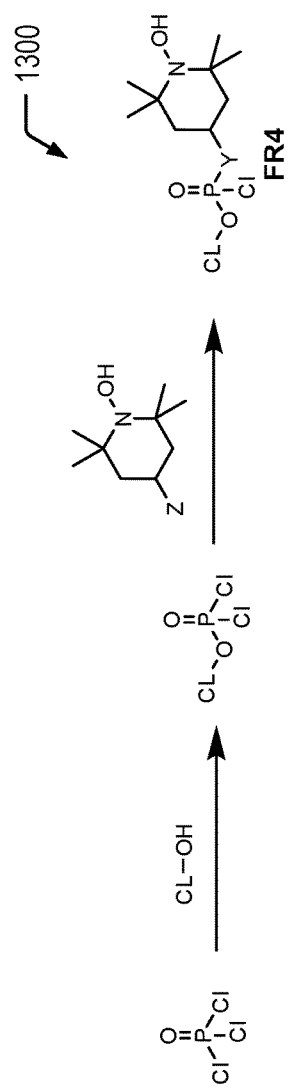
FIG. 13 is a chemical reaction diagram illustrating an example of a process of forming the fourth FR molecule depicted in FIG. 4B, according to one embodiment.

Referring to FIG. 13, a chemical reaction diagram 1300 illustrates an example of a process of forming the FR4 molecule depicted in FIG. 4B, according to one embodiment. The FR4 molecule represents an example of a molecule that includes a phosphoryl group (i.e., a phosphorus-oxygen double bond), a chloride group, an aryloxy group (including a piperidine ring), and one CL moiety. As illustrated in FIG. 4B, the chloride group may react with a functional group (represented as Y) of the functionalized TMP derivative molecule depicted on the left side of the chemical reaction diagram 410 to form the fourth FR-HALS molecule depicted on the right side of the chemical reaction diagram 410. As illustrated and previously described herein with respect to FIG. 4A, the CL moiety may include an allyl, furan, epoxide, carbonate, or imide functional group (among other alternatives).

FIG. 13 illustrates that an alcohol containing one of the CL moieties (identified as "CL-OH" in FIG. 13) and phosphoryl chloride ($POCl_3$) may be utilized to form the FR4 molecule. As a prophetic example, CL-OH (1 equiv.) which may be dissolved in diethyl ether, THF, or DCM may be slowly added to a mixture of $POCl_3$ (1 equiv.) and triethylamine (1.1 equiv.) in ether, THF, or DCM at 0-5° C. under nitrogen atmosphere. The reaction may be heated to reflux for 6 h or more. Triethylamine hydrochloride may be filtered and the filtrate may be concentrated in vacuo, and purified by fractional distillation. The TMP Compound" (1 equiv.) which may be dissolved in diethyl ether, THF, or DCM may be slowly added to a mixture of alkyl- or aryl-phosphonic dichloride (1 equiv.) and triethylamine (1.1 equiv.) in ether, THF, or DCM at 0-5° C. under nitrogen atmosphere. The reaction may be heated to reflux for 6 h or more. Triethylamine hydrochloride may be filtered and the filtrate may be concentrated in vacuo, and purified by fractional distillation.

Figure 14:
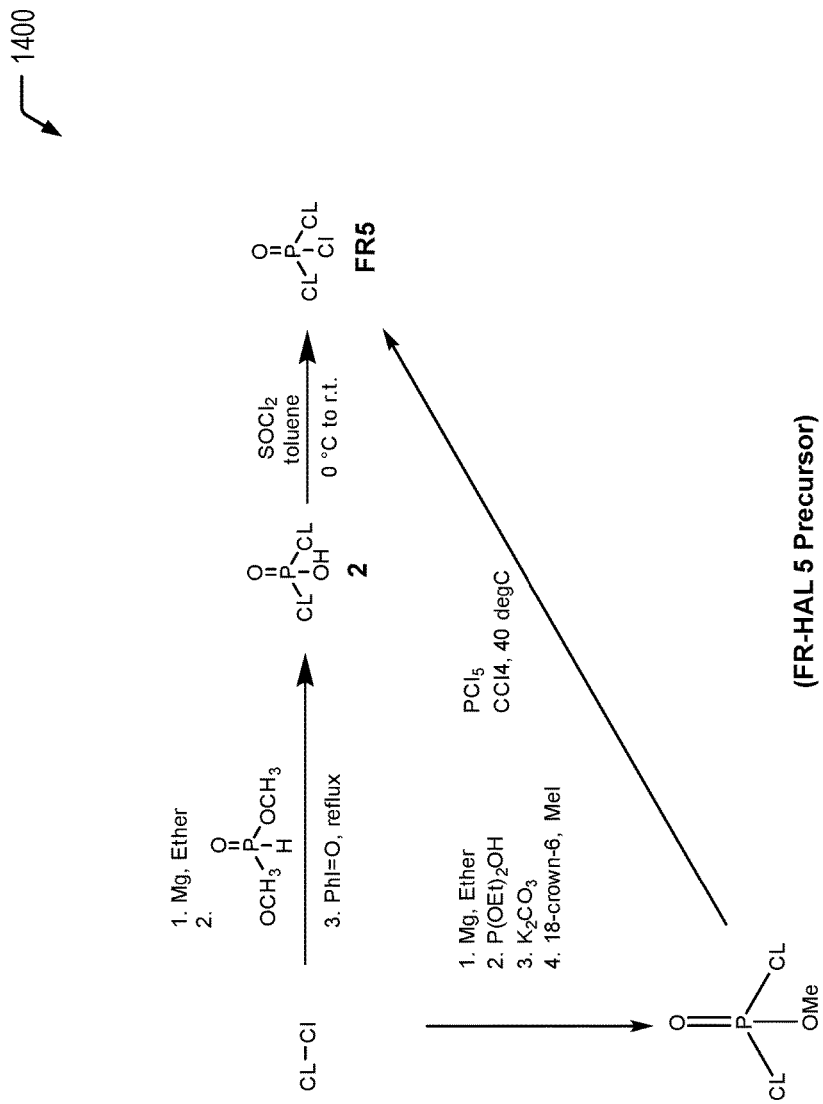
FIG. 14 is a chemical reaction diagram illustrating examples of alternative processes of forming the fifth FR molecule depicted in FIG. 5B, according to one embodiment.

Referring to FIG. 14, a chemical reaction diagram 1400 illustrates examples of alternative processes of forming the FR5 molecule depicted in FIG. 5B, according to one embodiment. The FR5 molecule represents an example of a molecule that includes a phosphoryl group (i.e., a phosphorus-oxygen double bond), a chloride group, and two CL moieties. As illustrated in FIG. 5B, the chloride group may react with a functional group (represented as Y) of the functionalized TMP derivative molecule depicted on the left side of the chemical reaction diagram 510 to form the fifth FR-HALS molecule depicted on the right side of the chemical reaction diagram 510. As illustrated and previously described herein with respect to FIG. 5A, the CL moieties may include allyl, furan, epoxide, carbonate, or imide functional groups (among other alternatives).

In the first example illustrated in FIG. 14, the FR5 molecule may be synthesized according to the following prophetic procedure. To a stirred suspension of activated magnesium turnings in diethyl ether may be added "CL-Cl", dropwise, at 0° C. Upon completion of the addition, the reaction mixture may be heated to reflux for 1 hour. The reaction mixture may then be cooled to room temperature and may be added via cannula to a stirred solution of phosphonic acid diethyl ester at 0° C. The reaction mixture may be warmed to room temperature and stirred until completion, poured into water, and extracted with diethyl ether. The combined organic fractions may be dried over $MgSO_4$, filtered, and the solvents removed in vacuo. The product may be purified by distillation or recrystallization. The phosphine oxide product may be added to a suspension of PhIO in an organic solvent that may include THF or toluene. The reaction mixture may be stirred for 20 minutes to 12 hours at reflux. The reaction mixture may then be diluted with ether and extracted of 5% $NaHCO_3$ water solution. The organic layer may be dried over $MgSO_4$, evaporated and separated by chromatography. The water layer may be acidified with concentrated HCl and extracted with ether. The combined ether solutions may be dried over $MgSO_4$, filtered and evaporated to yield the product. The bis(methyl)furan phosphine oxide may be added, dropwise, to an excess of thionyl chloride (or oxalyl chloride, or isocyanuric chloride) at 0° C. The reaction mixture may be warmed to ambient temperature or reflux and stirred until completion as indicated by TLC. The excess thionyl chloride may be removed in vacuo and the crude product may be purified by fractional distillation.

In the second example illustrated in FIG. 14, the FR5 molecule may be synthesized according to the following prophetic procedure. To a stirred suspension of activated magnesium turnings in diethyl ether may be added "CL-Cl", dropwise, at 0° C. Upon completion of the addition, the reaction mixture may be heated to reflux for 1 hour. The reaction mixture may then be cooled to room temperature and may be added via cannula to a stirred solution of phosphonic acid diethyl ester at 0° C. The reaction mixture may be warmed to room temperature and stirred until completion, poured into water, and extracted with diethyl ether. The combined organic fractions may be dried over $MgSO_4$, filtered, and the solvents removed in vacuo. The product may be purified by distillation or recrystallization. The phosphinic acid product may be stirred with a suspension of potassium carbonate in an organic solvent such as DMF or THF and heated to a temperature that may be between 60-100° C. Methyl iodide and 18-crown-6 may be added dropwise to the reaction mixture, and may be stirred until completion. The reaction mixture may be poured into water, and extracted with diethyl ether. The combined organic fractions may be dried over $MgSO_4$, filtered, and the solvents removed in vacuo. The product may be purified by distillation or recrystallization. To a solution of the product from the previous step in $CCl_4$ may be added $PCl_5$ (excess) at 0° C. under an inert atmosphere. The mixture may be allowed to warm to room temperature and may be stirred for an additional day. The solvent may be removed in vacuo and the residue may be distilled to give the product.

Figure 15:
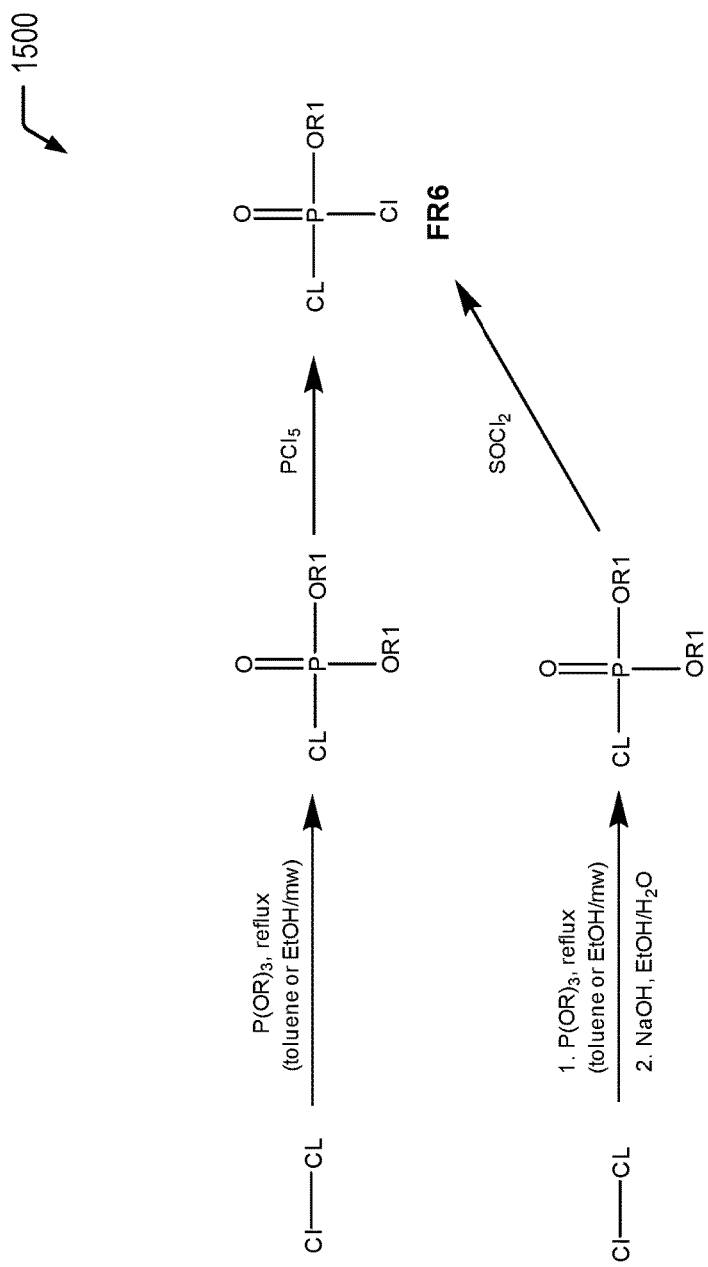
FIG. 15 is a chemical reaction diagram illustrating examples of alternative processes of forming the sixth FR molecule depicted in FIG. 6B, according to one embodiment.

Referring to FIG. 15, a chemical reaction diagram 1500 illustrates examples of alternative processes of forming the FR6 molecule depicted in FIG. 6B, according to one embodiment. The FR6 molecule represents an example of a molecule that includes a phosphoryl group (i.e., a phosphorus-oxygen double bond), a chloride group, an alkoxy/aryloxy group (O—R1), and one CL moiety. As illustrated in FIG. 6B, the chloride group may react with a functional group (represented as Y) of the functionalized TMP derivative molecule depicted on the left side of the chemical reaction diagram 610 to form the sixth FR-HALS molecule depicted on the right side of the chemical reaction diagram 610. As illustrated and previously described herein with respect to FIG. 6A, the CL moiety may include an allyl, furan, epoxide, carbonate, or imide functional group (among other alternatives).

In the first example illustrated in FIG. 15, the FR6 molecule may be synthesized according to the following prophetic procedure. CL-Cl (1 equiv.) and trialkyl phosphite may be added to a reaction vessel, which may include an organic solvent such as toluene, THF, ethanol, or DMF, and may also contain a compound such as alumina. The reaction may be heated to reflux or up to 180° C. if done using neat conditions. The reaction mixture may also be irradiated by microwaves for a short period to increase the reaction rate. The reaction may be cooled to room temperature and the excess trialkyl phosphite may be removed in vacuo or it may be washed with DCM, and dried for $CaCl_2$ prior to filtration and having the solvents removed in vacuo. The phosphonate may be purified by fractional distillation. To a solution of the phosphonate product may be added $PCl_5$ (excess) at 0° C. under an inert atmosphere. The reaction may be performed in a solvent such as $CCl_4$. The mixture may be allowed to warm to room temperature and may be stirred for an additional day. The solvent may be removed in vacuo and the residue may be distilled to give the product.

In the second example illustrated in FIG. 15, the FR6 molecule may be synthesized according to the following procedure. CL-Cl (1 equiv.) and trialkyl phosphite may be added to a reaction vessel, which may include an organic solvent such as toluene, THF, ethanol, or DMF, and may also contain a compound such as alumina. The reaction may be heated to reflux or up to 180° C. if done using neat conditions. The reaction mixture may also be irradiated by microwaves for a short period to increase the reaction rate. The reaction may be cooled to room temperature and the excess trialkyl phosphite may be removed in vacuo or it may be washed with DCM, and dried for $CaCl_2$ prior to filtration and having the solvents removed in vacuo. The phosphonate may be purified by fractional distillation. was refluxed in 50 mL of ethanolic sodium hydroxide (g) for 12 hours, and most of the ethanol was removed by distillation. The reaction mixture may be diluted with 30 mL of $H_2O$, acidified, and extracted with $CHCl_3$, and then the oil layer may be separated and dried over $Na_2SO_4$. The $CHCl_3$ may be distilled under reduced pressure. The residual materials may be slowly crystallized in a refrigerator to obtain compound. Thionyl chloride ($SOCl_2$) (excess) may be added to a solution of the phosphonic acid product at 0° C. The mixture may be allowed to warm to room temperature, or heated to 40° C. and may be stirred for an additional day. The solvent is removed in vacuo and the residue may be distilled to give the product.

Referring to FIG. 16, a chemical reaction diagram 1600 illustrates an example of a process of forming the seventh FR7 molecule depicted in FIGS. 7B and 9B, according to one embodiment. The FR7 molecule represents an example of a molecule that includes a phosphoryl group (i.e., a phosphorus-oxygen double bond), a chloride group, an alkyl/aryl group (R1), and one CL moiety.

As illustrated in the example of FIG. 7B, the chloride group may react with a functional group (represented as Y) of the functionalized TMP derivative molecule depicted on the left side of the chemical reaction diagram 710 to form the seventh FR-HALS molecule depicted on the right side of the chemical reaction diagram 710. As illustrated and previously described herein with respect to FIG. 7A, the CL moiety may include an allyl, furan, epoxide, carbonate, or imide functional group (among other alternatives).

As illustrated in the example of FIG. 9B, the chloride group may react with an amine group (NH) of the functionalized TMP derivative molecule depicted on the left side of the chemical reaction diagram 910 to form the ninth FR-HALS molecule depicted on the right side of the chemical reaction diagram 910. As illustrated and previously described herein with respect to FIG. 9A, the CL moiety may include an allyl, furan, epoxide, carbonate, or imide functional group (among other alternatives).

FIG. 16 illustrates that the FR7 molecule may be formed according to the following prophetic procedure. To a stirred suspension of activated magnesium turnings in diethyl ether may be added "CL-Cl", dropwise, at 0° C. Upon completion of the addition, the reaction mixture may be heated to reflux for 1 hour. The reaction mixture may then be cooled to room temperature and may be added via cannula to a stirred solution of alkyl or arylphosphinic dichloride at 0° C. The reaction mixture may be warmed to room temperature and stirred until completion, poured into an aqueous NaOH solution, and stirred overnight. The reaction mixture may be extracted with diethyl ether and the combined organic fractions may be dried over $MgSO_4$, filtered, and the solvents removed in vacuo. The product may be purified by distillation. Oxalyl chloride (excess) may be added to a solution of the product from the previous step at 0° C. The mixture may be allowed to warm to room temperature, or heated to 40° C. and may be stirred for an additional day. The solvent may be removed in vacuo and the residue may be distilled to give the product.

Referring to FIG. 17, a chemical reaction diagram 1700 illustrates an example of a process of forming the FR8 molecule depicted in FIG. 8B, according to one embodiment. The FR8 molecule represents an example of a molecule that includes a phosphoryl group (i.e., a phosphorus-oxygen double bond), a chloride group, an aryloxy group (including a piperidine ring), and one CL moiety. As illustrated in FIG. 8B, the chloride group may react with a functional group (represented as Y) of the functionalized TMP derivative molecule depicted on the left side of the chemical reaction diagram 810 to form the eighth FR-HALS molecule depicted on the right side of the chemical reaction diagram 810. As illustrated and previously described herein with respect to FIG. 8A, the CL moiety may include an allyl, furan, epoxide, carbonate, or imide functional group (among other alternatives).

FIG. 17 illustrates that the FR8 molecule may be formed according to the following prophetic procedure. A mixture of phosphorus trichloride (1 equiv.), anhydrous aluminum chloride (1 equiv.) and "CL-Cl" (1 equiv.) may be heated to reflux until complete dissolution/disappearance of aluminum chloride or completion of the reaction. After cooling to −10° C., excess methylene chloride, and water (10 equiv.) may be subsequently added slowly dropwise. The solids may be removed by filtration, and the solvent may be removed in vacuo. The crude product may be purified by fractional distillation to yield the mono-functionalized phosphinic dichloride. The TMP Compound (1 equiv.) which may be dissolved in diethyl ether, THF, or DCM may be slowly added to a mixture of the phosphinic dichloride (1 equiv.) from the previous step and triethylamine (1.1 equiv.) in ether, THF, or DCM at 0-5° C. under nitrogen atmosphere. The reaction may be heated to reflux for 6 hours or more. Triethylamine hydrochloride may be filtered, and the filtrate may be concentrated in vacuo, and purified by fractional distillation.

Figure 18:
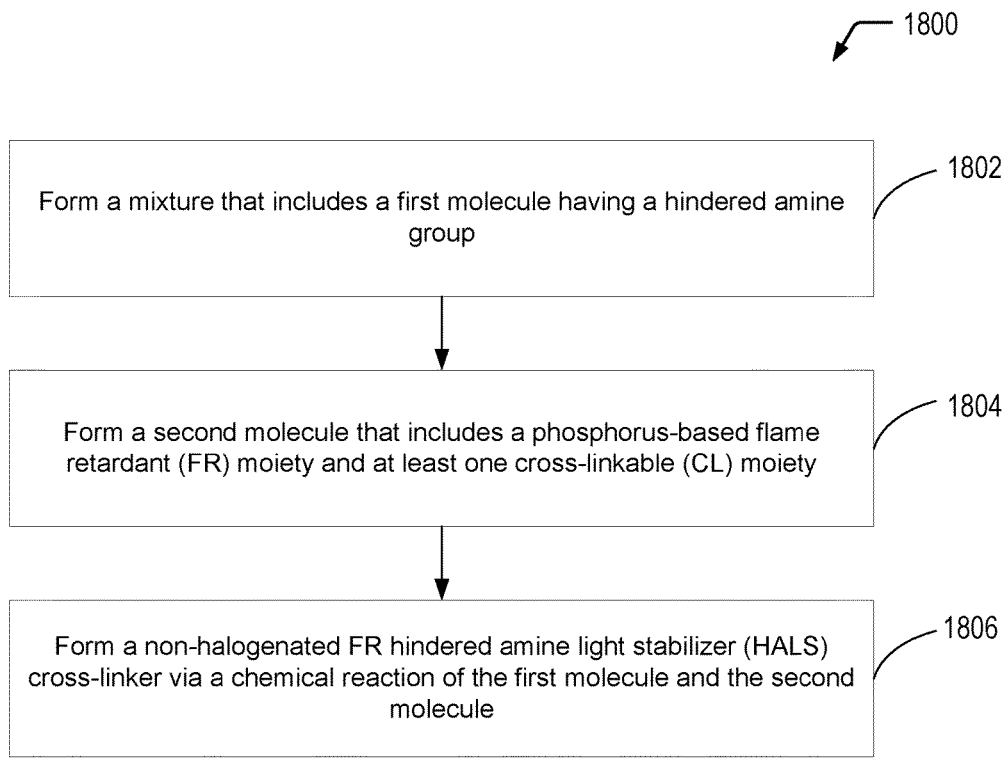
FIG. 18 is a flow diagram illustrating a particular embodiment of a process of forming a non-halogenated FR HALS cross-linker of the present disclosure.

Referring to FIG. 18, a flow diagram illustrates an example of a process 1800 of forming a non-halogenated FR HALS cross-linker, according to one embodiment. It will be appreciated that the operations shown in FIG. 18 are for illustrative purposes only and that the operations may be performed in alternative orders, at alternative times, by a single entity or by multiple entities, or a combination thereof. As an example, one entity may form/provide a first molecule having a hindered amine group (illustrated as operation 1802), while another entity may form a second molecule that includes a phosphorus-based FR moiety and one or more CL moieties (illustrated as operation 1804). In some cases, yet another entity may utilize the first molecule and the second molecule for form the non-halogenated FR HALS cross-linker (illustrated as operation 1806). Further, while not shown in the example of FIG. 18, the same entity or a different entity may utilize the non-halogenated FR HALS cross-linker to impart flame retardancy and light stabilization characteristics to a polymeric material.

The process 1800 includes forming a mixture that includes a first molecule having a hindered amine group, at 1802. For example, the first molecule having the hindered amine group may correspond to the first molecule depicted on the left side of each of the chemical reaction diagrams 110, 210, 310, 410, 510, 610, 710, 810, and 910 depicted in FIGS. 1B to 9B.

The process 1800 includes forming a second molecule that includes a phosphorus-based FR moiety and one or more CL moieties, at 1804. For example, the FR molecules FR1, FR2, FR3, FR4, FR5, FR6, FR7, and FR8 depicted in FIGS. 1B to 9B may be formed according to one of the processes described further herein with respect to FIGS. 10 to 17. In each case, utilizing phosphorus-based materials rather than halogenated (e.g., brominated) materials to impart flame retardancy characteristics may reduce or eliminate the loss of light stabilization associated with the release of bromine radicals from conventional brominated flame retardant additives.

The process 1800 includes forming a non-halogenated FR HALS cross-linker via a chemical reaction of the first molecule and the second molecule, at 1806. For example, the nine example FR-HALS molecules depicted in FIGS. 1A to 9A may be formed according to one of the processes described further herein with respect to FIGS. 1B to 9B, respectively.

Thus, FIG. 18 illustrates an example of a process of forming a non-halogenated FR HALS cross-linker. The non-halogenated FR HALS cross-linkers of the present disclosure may be utilized to impart flame retardancy and light stabilization properties to a polymeric material. In some cases, the non-halogenated FR HALS cross-linkers of the present disclosure may be utilized as a multi-function additive to a polymeric material. In other cases, as described further herein with respect to FIG. 19, the non-halogenated FR HALS cross-linker of the present disclosure may be chemically bonded to a polymer chain via a chemical reaction at the hindered amine location. Further, the CL moiety(s) may enable the non-halogenated FR HALS cross-linker to be bonded to one or more additional polymer chains to form a flame retardant, light stabilized, cross-linked polymeric material.

Figure 19:
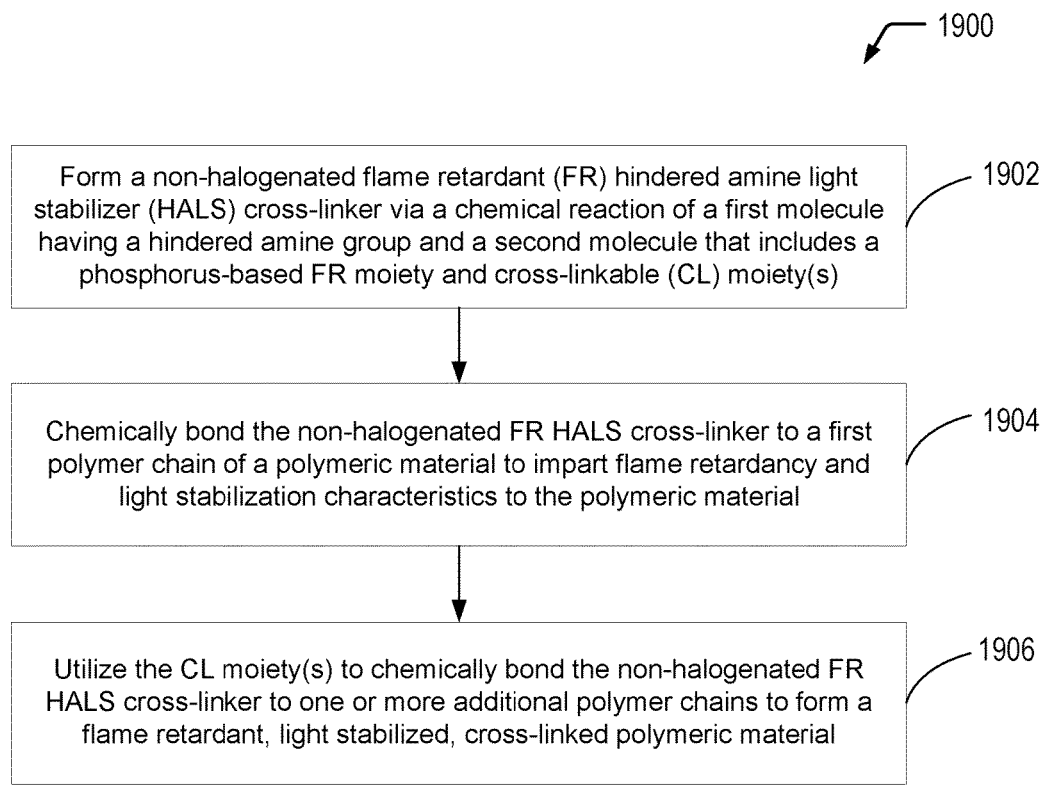
FIG. 19 is a flow diagram illustrating a particular embodiment of a process of utilizing a non-halogenated FR HALS cross-linker of the present disclosure to form a cross-linked, light stabilized, flame retardant polymeric material.

Referring to FIG. 19, a flow diagram illustrates a particular embodiment of a process 1900 of utilizing a non-halogenated FR HALS cross-linker of the present disclosure to form a cross-linked, light stabilized, flame retardant polymeric material. It will be appreciated that the operations shown in FIG. 19 are for illustrative purposes only and that the operations may be performed in alternative orders, at alternative times, by a single entity or by multiple entities, or a combination thereof. As an example, one entity may form the non-halogenated FR HALS cross-linker (illustrated as operation 1902). In some cases, another entity may utilize the non-halogenated FR HALS cross-linker to impart flame retardancy and light stabilization characteristics to a polymeric material (illustrated as operation 1904) and to cross-link the polymeric material (illustrated as operation 1906).

The process 1900 includes forming a non-halogenated FR HALS cross-linker, at 1902. Forming the non-halogenated HALS cross-linker includes chemically reacting a first molecule having a hindered amine group and a second molecule that includes a phosphorus-based FR moiety and CL moiety(s). For example, the nine example FR-HALS molecules depicted in FIGS. 1A to 9A may be formed according to one of the processes described further herein with respect to FIGS. 1B to 9B, respectively.

The process 1900 includes chemically bonding the non-halogenated FR HALS cross-linker to a first polymer chain of a polymeric material, at 1904. The non-halogenated FR HALS cross-linker imparts flame retardancy and light stabilization characteristics to the polymeric material. In a particular embodiment, where N—X of the particular cross-linkable FR-HALS molecule corresponds to a nitroxyl radical (N—O.), the radical may enable the non-halogenated FR HALS molecules of the present disclosure to be bonded to a variety of polymers or polymeric blends. As an example, the nitroxyl radical may enable a non-halogenated FR HALS molecule of the present disclosure to be chemically bonded to a first polymer chain (at position 1 of the six-membered ring).

In the particular embodiment depicted in FIG. 19, the process 1900 further includes utilizing the CL moiety(s) to chemically bond the non-halogenated FR HALS cross-linker to one or more additional polymer chains, at 1906. Chemically bonding the non-halogenated FR HALS cross-linker to the additional polymer chain(s) results in the formation of a flame retardant, light stabilized, cross-linked polymeric material. For example, the one or more CL moieties (linked to the carbon atom at position 4 of the six-membered ring in each of FR-HALS molecules of the present disclosure) may further enable the non-halogenated FR HALS molecule to be chemically bonded to one or more additional polymer chains, thereby cross-linking the first polymer chain to the additional polymer chain(s).

Thus, FIG. 19 illustrates an example of a process of utilizing a non-halogenated FR HALS cross-linker of the present disclosure to form a cross-linked, light stabilized, flame retardant polymeric material. In the example of FIG. 19, the non-halogenated FR HALS cross-linker may be chemically bonded to a first polymer chain (e.g., via a chemical reaction at the hindered amine location). Further, the CL moiety(s) may enable the non-halogenated FR HALS cross-linker to be bonded to one or more additional polymer chains to form a flame retardant, light stabilized, cross-linked polymeric material.

It will be understood from the foregoing description that modifications and changes may be made in various embodiments of the present invention without departing from its true spirit. The descriptions in this specification are for purposes of illustration only and are not to be construed in a limiting sense. The scope of the present invention is limited only by the language of the following claims.

What is claimed is:

1. A process of forming a non-halogenated flame retardant (FR) hindered amine light stabilizer (HALS) cross-linker, the process comprising:
forming a mixture that includes a flame retardant (FR) molecule including a phosphoryl group, a chloride group, and at least one allyl group; and
forming a non-halogenated FR hindered amine light stabilizer (HALS) cross-linker via a chemical reaction of the FR molecule and a functionalized 2,2,6,6-tetramethylpiperidine (TMP) molecule having the following formula:

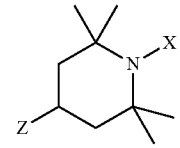

wherein X corresponds to an oxyl radical (O.), and wherein Z corresponds to a hydroxyl (OH) group.

2. The process of claim 1, wherein the at least one allyl group includes a single allyl group.

3. The process of claim 1, wherein the at least one allyl group includes two allyl groups.

* * * * *